(12) United States Patent
Furer et al.

(10) Patent No.: US 10,138,246 B2
(45) Date of Patent: Nov. 27, 2018

(54) DEUTERATED TRIAZOLOPYRIDAZINE AS A KINASE MODULATOR

(71) Applicant: Janssen Pharmaceutica NV, Beerse (BE)

(72) Inventors: Patrick Blasius Furer, Kaiseraugst (CH); Ronaldus Arnodus Hendrika Joseph Gilissen, Beerse (BE); Ioannnis Nicolaos Houpis, Beerse (BE); Lieven Meerpoel, Beerse (BE); Timothy Pietro Suren Perera, Oxford (GB); Philip James Pye, Beerse (BE)

(73) Assignee: Janssen Pharmaceutica NV, Beerse (BE)

( * ) Notice: Subject to any disclaimer, the term of this patent is extended or adjusted under 35 U.S.C. 154(b) by 0 days.

(21) Appl. No.: 15/531,780

(22) PCT Filed: Dec. 3, 2015

(86) PCT No.: PCT/EP2015/078525
§ 371 (c)(1),
(2) Date: May 31, 2017

(87) PCT Pub. No.: WO2016/087586
PCT Pub. Date: Jun. 9, 2016

(65) Prior Publication Data
US 2017/0267684 A1 Sep. 21, 2017

(30) Foreign Application Priority Data

Dec. 4, 2014 (EP) .................................... 14196387
Dec. 5, 2014 (EP) .................................... 14196585

(51) Int. Cl.
| | | |
|---|---|---|
| *C07D 487/04* | (2006.01) | |
| *A61K 31/5025* | (2006.01) | |
| *C07B 59/00* | (2006.01) | |
| *A61K 45/06* | (2006.01) | |

(52) U.S. Cl.
CPC ........ *C07D 487/04* (2013.01); *A61K 31/5025* (2013.01); *A61K 45/06* (2013.01); *C07B 59/002* (2013.01); *C07B 2200/05* (2013.01)

(58) Field of Classification Search
CPC .................................................. C07D 487/04
See application file for complete search history.

(56) References Cited

U.S. PATENT DOCUMENTS

| | | |
|---|---|---|
| 5,474,765 A | 12/1995 | Thorpe et al. |
| 5,762,918 A | 6/1998 | Thorpe et al. |
| 5,855,866 A | 1/1999 | Thorpe et al. |
| 6,342,219 B1 | 1/2002 | Thorpe et al. |
| 6,776,796 B2 | 8/2004 | Falotico et al. |
| 2002/0016625 A1 | 2/2002 | Falotico et al. |

FOREIGN PATENT DOCUMENTS

| | | |
|---|---|---|
| WO | WO9632907 A1 | 10/1996 |
| WO | WO2007075567 A1 | 7/2007 |
| WO | WO2008155378 A1 | 12/2008 |
| WO | WO2011135376 A1 | 11/2011 |
| WO | WO2013061080 A1 | 5/2013 |

OTHER PUBLICATIONS

Lolkema et al. Clin Cancer Res. May 15, 2015; 21(10): 2297-2304.*
International Search Report and Written Opinion dated Jan. 29, 2016 for PCT/EP2015/078525 Filed Dec. 3, 2015. pp. 1-8.
International J. Pharm. 1986, 33, 201-217; J. Pharm Sci., Jan. 1977, 66(1), p. 1), Gould.
IUPAC Recommendations for Fundamental Stereochemistry (Section E), Pure Appl. Chem., 1976, 45:13-30.
Simpson WG, The calcium channel blocker verapamil and cancer chemotherapy. Cell Calcium. Dec. 1985; 6 (6):449-67.
Schiele TM, et al., 2004, "Vasular restenosis-striving for therapy." Expert Opin Pharmacother 5(11):2221-32.

(Continued)

Primary Examiner — Emily A Bernhardt
(74) Attorney, Agent, or Firm — Dinsmore & Shohl LLP

(57) ABSTRACT

The invention is directed to a triazolopyridazine compound of formula (I), N-oxides, pharmaceutically acceptable salts and solvates thereof, wherein D represents deuterium, the use of such compounds as protein tyrosine kinase modulators, particularly inhibitors of c-Met, and the use of such compounds to reduce or inhibit kinase activity of c-Met in a cell or a subject, and modulate c-Met expression in a cell or subject, and the use of such compounds for preventing or treating in a subject a cell proliferative disorder and/or disorders related to c-Met. The present invention is further directed to pharmaceutical compositions comprising the compounds of the present invention and to methods for treating conditions such as cancers and other cell proliferative disorders.

(I)

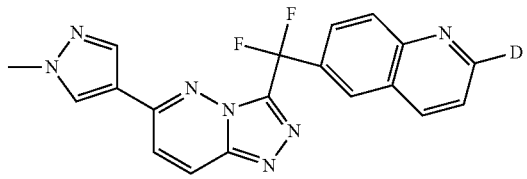

17 Claims, 2 Drawing Sheets

(56) References Cited

OTHER PUBLICATIONS

Figure 1A:
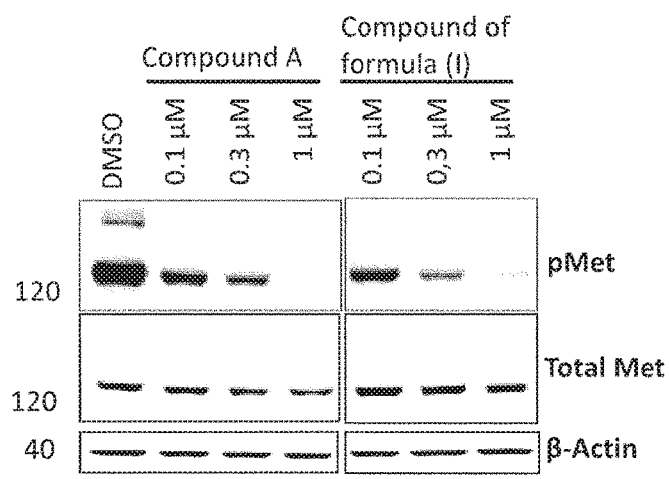

Taher et al., "Hepatocyte growth factor triggers signaling cascades mediating vascular smooth muscle cell migration". Biochem Biophys Res Commun. (2002) 298(1):80-6.
Morishita R, Aoki M., Yo Y, Ogihara T., "Hepatocyte growth factor as cardiovascular hormone: role of HGF in the pathogenesis of cardiovascular disease." Endocr J. Jun. 2002; 49(3):273-84.
Amon, et al., "Monoclonal Antibodies for Immunotargeting of Drugs in Cancer Therapy", in Monoclonal Antibodies and Cancer Therapy, Reisfeld et al. (eds.) pp. 243-256 (Alan R. Liss, Inc. 1985).
Hellstrom et al., "Antibodies for Drug Delivery", in Controlled Drug Delivery (2nd Ed.), Robinson et al., (eds.), pp. 623-653 (Marcel Dekker, Inc. 1987).
Shao et al., "The Kinetic Isotope Effect in the Search for Deuterated Drugs", Drug News and Perspectives, Prous Science, Jan. 1, 2010, pp. 398-404.
Fisher et al., "The complexities inherent in attempts to decrease drug clearance by blocking sites of CYP-mediated metabolism", Current Opinion in Drug Discovery and Development, Current Drugs, Jan. 1, 2006, pp. 101-109.
Thorpe, P.E., "Antibody Carriers of Cytotoxic Agents in Cancer Therapy: A Review", Monoclonal Antibodies '84: Biological and Clinical Operations, (1985) pp. 475-506.

\* cited by examiner

Western blotting for EBC-1. Cells incubated with the compounds at indicated doses for 24h pMet protein levels normalized to actin in EBC-1 cells after treatment with compounds Western blotting for Snu-5. Cells incubated with the compounds at indicated doses for 24h pMet protein levels normalized to actin in Snu-5 cells after treatment with compounds

DEUTERATED TRIAZOLOPYRIDAZINE AS A KINASE MODULATOR

FIELD OF THE INVENTION

The invention relates to a novel compound that functions as a protein tyrosine kinase modulator. More particularly, the invention relates to a novel compound that functions as an inhibitor of c-Met.

BACKGROUND OF THE INVENTION

The present invention relates to a triazolopyridazine as an inhibitor of tyrosine kinases, including c-Met. Triazolopyridazines have been reported with useful therapeutic properties including in WO2007/075567.

Protein kinases are enzymatic components of the signal transduction pathways that catalyze the transfer of the terminal phosphate from ATP to the hydroxy group of tyrosine, serine and/or threonine residues of proteins. Thus, compounds that inhibit protein kinase functions are valuable tools for assessing the physiological consequences of protein kinase activation. The overexpression or inappropriate expression of normal or mutant protein kinases in mammals has been a topic of extensive study and has been demonstrated to play a significant role in the development of many diseases, including diabetes, angiogenesis, psoriasis, restenosis, ocular diseases, schizophrenia, rheumatoid arthritis, atherosclerosis, cardiovascular disease and cancer. The cardiotonic benefit of kinase inhibition has also been studied. In sum, inhibitors of protein kinases have particular utility in the treatment of human and animal disease.

The hepatocyte growth factor (HGF) (also known as scatter factor (SF)) receptor, c-Met, is a receptor tyrosine kinase that regulates cell proliferation, morphogenesis, and motility. The c-Met gene is translated into a 170 kD protein that is processed into a cell surface receptor composed of a 140 kD beta transmembrane subunit and 50 kD glycosylated extra cellular alpha subunit.

Mutations in c-Met, over-expression of c-Met and/or HGF/SF, expression of c-Met and HGF/SF by the same cell, and overexpression and/or aberrant c-Met signaling is present in a variety of human solid tumors and is believed to participate in angiogenesis, tumor development, invasion, and metastasis.

Cell lines with uncontrolled c-Met activation, for example, are both highly invasive and metastatic. A notable difference between normal and transformed cells expressing c-Met receptor is that phosphorylation of the tyrosine kinase domain in tumor cells is often independent of the presence of ligand.

C-Met mutations/alterations have been identified in a number of human diseases, including tumors and cancers—for instance, hereditary and sporadic human papillary renal carcinomas, breast cancer, colorectal cancer, gastric carcinoma, glioma, ovarian cancer, hepatocellular carcinoma, head and neck squamous cell carcinomas, testicular carcinoma, basal cell carcinoma, liver carcinoma, sarcoma, malignant pleural mesothelioma, melanoma, multiple myeloma, osteosarcoma, pancreatic cancer, prostate cancer, synovial sarcoma, thyroid carcinoma, non-small cell lung cancer (NSCLC) and small cell lung cancer, transitional cell carcinoma of urinary bladder, testicular carcinoma, basal cell carcinoma, liver carcinoma—and leukemias, lymphomas, and myelomas—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocyctic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma, non-Hodgkin's lymphoma and Hodgkin's disease (also called Hodgkin's lymphoma).

Because of the role of aberrant HGF/SF—Met signaling in the pathogenesis of various human cancers, inhibitors of c-Met receptor tyrosine kinase have broad applications in the treatment of cancers in which Met activity contributes to the invasive/metastatic phenotype, including those in which c-Met is not overexpressed or otherwise altered. Inhibitors of c-Met also inhibit angiogenesis and therefore are believed to have utility in the treatment of diseases associated with the formation of new vasculature, such as rheumatoid arthritis, retinopathy.

Over-expression of c-Met is also believed to be a potentially useful predictor for the prognosis of certain diseases, such as, for example, breast cancer, non-small cell lung carcinoma, pancreatic endocrine neoplasms, prostate cancer, esophageal adenocarcinoma, colorectal cancer, salivary gland carcinoma, diffuse large B-cell lymphoma and endometrial carcinoma.

Many strategies have been devised to attenuate aberrant Met signaling in human tumors. Some of these strategies include the use of HGF antagonists and small-molecule inhibitors.

The safety, pharmacokinetics, pharmacodynamics and initial efficacy of the potent and selective c-Met inhibitor with the following structure

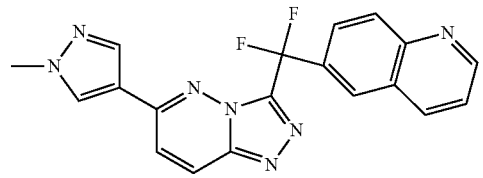 [SMILES: Cn1cc(-c2ccc3nnc(C(F)(F)c4ccc5ncccc5c4)n3n2)cn1]

(hereinafter referred to as compound A)
was explored in a phase I, first-in-human trial. This led to the detection of unexpected renal toxicity. These data contradicted pre-clinical tests showing a clean toxicity profile in rat and dog. Extensive additional pre-clinical experiments were performed to understand the nature of the renal effects. Metabolism data pointed into the direction of the rabbit to be a suitable toxicology species. A toxicology study in rabbit showed that compound A did affect renal function and histological analysis revealed crystal formation with consequently degenerative and inflammatory changes in the kidney. Further investigation suggested an aldehyde oxidase-dependent, species-specific, generation of insoluble metabolites that cause kidney damage through crystal formation in the renal tubules. The following metabolites were found to form crystals:

Metabolite 1:

6-{Difluoro[6-(1H-pyrazol-4-yl)[1,2,4]triazolo[4,3-b]pyridazin-3-yl]methyl}quinolin-2(1H)-one.

Metabolite 2:

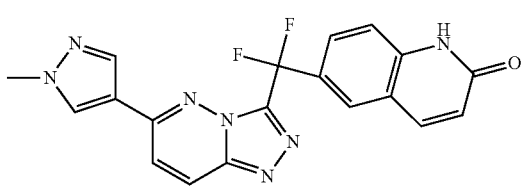 [SMILES: Cn1cc(-c2ccc3nnc(C(F)(F)c4ccc5[nH]c(=O)ccc5c4)n3n2)cn1]

6-{Difluoro[6-(1-methyl-H-pyrazol-4-yl)[1,2,4]triazolo[4,3-b]pyridazin-3-yl]methyl}quinolin-2(1H)-one.

Solubility of Metabolite 2:
at pH 4.84, solubility of 0.001 mg/ml
at pH 7.33, solubility of 0.002 mg/ml.

Because no viable strategies were identified to circumvent the renal toxicity, further clinical development of compound A was abandoned.

SUMMARY OF THE INVENTION

The present invention provides a novel triazolopyridazine as a protein tyrosine kinase modulator, in particularly an inhibitor of c-Met, and the use of such compound to reduce or inhibit kinase activity of c-Met in a cell or a subject, and modulate c-Met expression in a cell or subject, and the use of such compound for preventing or treating in a subject a cell proliferative disorder and/or disorders related to c-Met. In particular, the present invention relates to said compound for use as a medicine, for use in the treatment of a cell proliferative disorder and/or a disorder related to c-Met. The present invention relates to said compound for use in the prevention or treatment, in particular treatment, of cancer, of a cell proliferative disorder and/or a disorder related to c-Met, or to the use of said compound for the manufacture of a medicament for the prevention or the treatment, in particular treatment, of cancer, a cell proliferative disorder and/or a disorder related to c-Met.

The present invention also relates to a pharmaceutical composition comprising the compound of the invention and a pharmaceutically acceptable carrier. Another aspect of the present invention is a pharmaceutical composition prepared by mixing the compound of the invention and a pharmaceutically acceptable carrier.

Other features and advantages of the invention will be apparent from the following detailed description of the invention and from the claims.

FIGURES

Figure 1B:
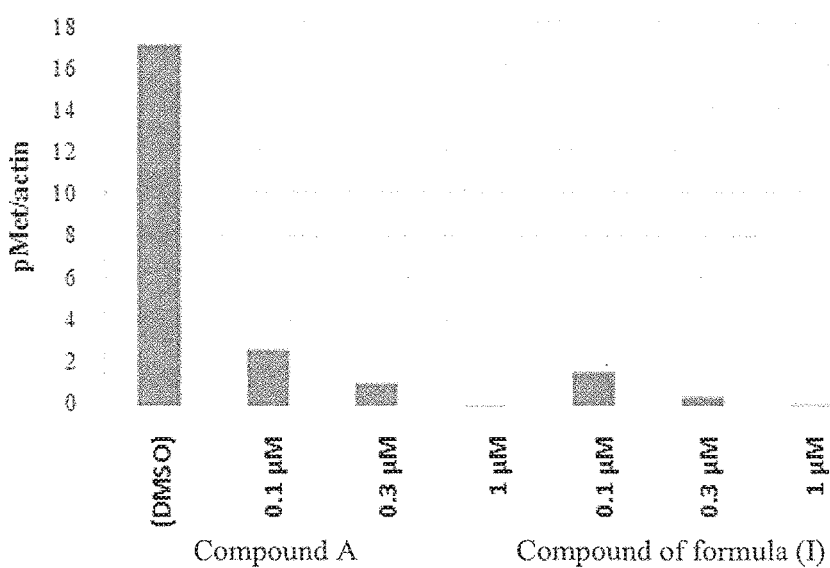
Figure 1C:
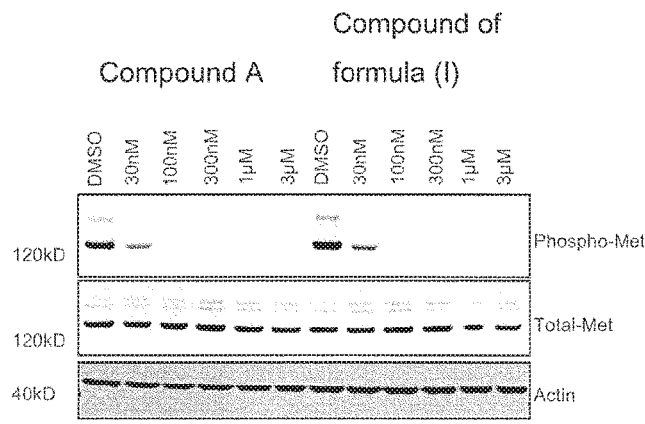
Figure 1D:
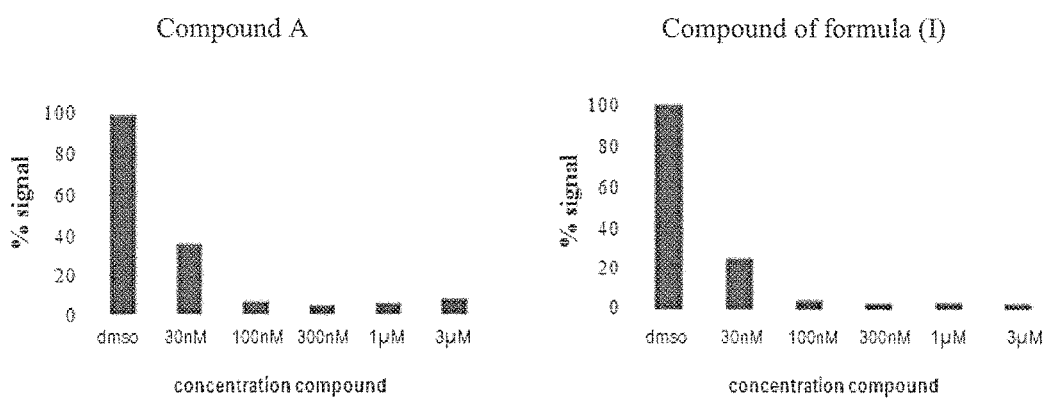

FIG. 1A: Western blot for EBC-1;
FIG. 1B: pMet protein levels normalized to actin in EBC-1 cells;
FIG. 1C: Western blot for Snu-5 B; and
FIG. 1D: pMet protein levels normalized to actin in Snu-5 cells.

DETAILED DESCRIPTION OF THE INVENTION

The present invention relates to the following compound of formula (I)

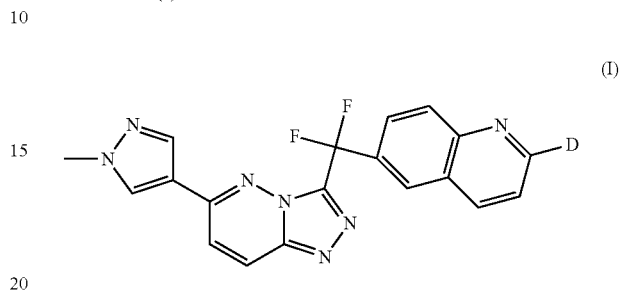

and N-oxides, pharmaceutically acceptable salts and solvates thereof, wherein D represents deuterium.

In an aspect, the present invention relates to the following compound of formula (I)

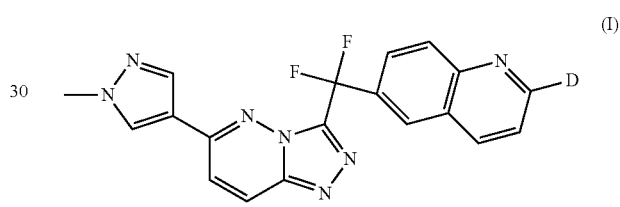

and pharmaceutically acceptable salts and solvates thereof, wherein D represents deuterium.

In an aspect, the present invention relates to the following compound of formula (I)

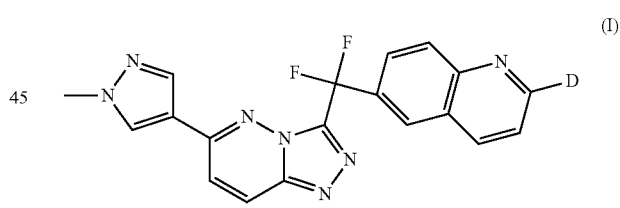

and pharmaceutically acceptable salts thereof, wherein D represents deuterium.

In an aspect, the present invention relates to the following compound of formula (I)

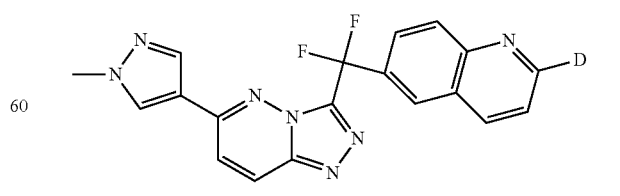

wherein D represents deuterium.

It will be recognized that some variation of natural isotopic abundance occurs in a synthesized compound depending upon the origin of chemical materials used in the synthesis. Thus, a preparation of compound A will inherently contain small amounts of deuterium. The concentration of such naturally occurring deuterium is small (natural abundance is 0.015%) and immaterial as compared to the content of deuterium of the compound of this invention.

The compound of the present invention is distinguished from such naturally occurring minor forms in that the term "compound" as used in this invention refers to a composition of matter wherein the abundance of deuterium is much higher than the natural abundance (0.015%), e.g. at least 1000 times higher (15%).

In an aspect of the invention, the compound of formula (I) has a deuterium content in 2-position of the quinoline (D) of at least 50% (D/H ratio at least 1:1), of at least 60%, of at least 70%, of at least 80%, of at least 90%, of at least 91%, of at least 92%, of at least 93%, of at least 94%, of at least 95%, of at least 96%, of at least 97%, of at least 98%, of at least 99%. Preferably the deuterium content in 2-position of the quinoline (D) is at least 93%, more preferably the deuterium content in 2-position of the quinoline (D) is at least 97% or 98%.

When a position is designated specifically as "H" or "hydrogen," or its chemical representation implies hydrogen, it is understood to have hydrogen at its natural abundance isotopic composition.

It was found that with the present compound of formula (I) the formation of insoluble/less soluble aldehyde oxidase mediated metabolites is down regulated. This may decrease renal toxicity.

Furthermore, it was found that there is a metabolisation switch for the present compound of formula (I) compared to the metabolisation of compound A (up regulation of CYP450 mediated metabolite formation). In case of the present compound of formula (I) more of the N-desmethyl metabolite with the following structure is formed

(an active metabolite) compared to the formation of the N-desmethyl metabolite with the following structure

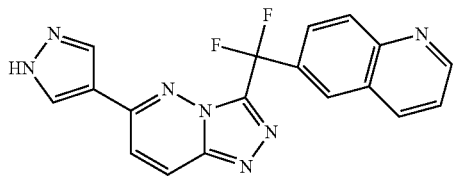 [SMILES: FC(F)(c1ccc2ncccc2c1)c1nnc2ccc(-c3cn[nH]c3)nn12]

upon administration of compound A. This may lower the therapeutically effective dose for the compound of formula (I) compared to compound A.

Further it was found that the compound of formula (I) also shows inhibition of the $^{14}$C-Metformin uptake in OCT2 cells.

As used hereinafter, the terms "compound of formula (I)" and "compounds of formula (I)" are meant to include also the N-oxides, pharmaceutically acceptable salts and solvates thereof.

Pharmaceutically Acceptably Salts

The compound of the present invention may also be present in the form of a pharmaceutically acceptable salt, in particular a pharmaceutically acceptable acid addition salt.

For use in medicines, the salts of the compounds of this invention refer to non-toxic "pharmaceutically acceptable salts." FDA approved pharmaceutically acceptable salt forms (Ref International J. Pharm. 1986, 33, 201-217; J. Pharm. Sci., 1977, January, 66(1), p1) include pharmaceutically acceptable acidic/anionic or basic/cationic salts.

Pharmaceutically acceptable acid addition salts include, and are not limited to acetate, benzenesulfonate, benzoate, bicarbonate, bitartrate, bromide, calcium edetate, camsylate, carbonate, chloride, citrate, dihydrochloride, edetate, edisylate, estolate, esylate, fumarate, glyceptate, gluconate, glutamate, glycollylarsanilate, hexylresorcinate, hydrabamine, hydrobromide, hydrochloride, hydroxynaphthoate, iodide, isethionate, lactate, lactobionate, malate, maleate, mandelate, mesylate, methylbromide, methylnitrate, methylsulfate, mucate, napsylate, nitrate, pamoate, pantothenate, phosphate/diphosphate, polygalacturonate, salicylate, stearate, subacetate, succinate, sulfate, tannate, tartrate, teoclate, tosylate and triethiodide. Organic or inorganic acids also include, and are not limited to, hydriodic, perchloric, sulfuric, phosphoric, propionic, glycolic, methanesulfonic, hydroxyethanesulfonic, oxalic, 2-naphthalenesulfonic, p-toluenesulfonic, cyclohexanesulfamic, saccharinic or trifluoroacetic acid. The pharmaceutically acceptable salts of the present invention also include stereochemically isomeric forms thereof.

Stereochemically Isomeric Forms

One skilled in the art will recognize that the compound of formula (I), in particular in case of salts, may have one or more asymmetric carbon atoms in its structure. It is intended that the present invention include within its scope single enantiomer forms of the compounds, racemic mixtures, and mixtures of enantiomers in which an enantiomeric excess is present.

The term "single enantiomer" as used herein defines all the possible homochiral forms which the compound of formula (I) may possess.

Stereochemically pure isomeric forms may be obtained by the application of art known principles. Diastereoisomers may be separated by physical separation methods such as fractional crystallization and chromatographic techniques, and enantiomers may be separated from each other by the selective crystallization of the diastereomeric salts with optically active acids or bases or by chiral chromatography. Pure stereoisomers may also be prepared synthetically from appropriate stereochemically pure starting materials, or by using stereoselective reactions.

The term "isomer" refers to compounds that have the same composition and molecular weight but differ in physical and/or chemical properties. Such substances have the same number and kind of atoms but differ in structure. The structural difference may be in constitution (geometric isomers) or in an ability to rotate the plane of polarized light (enantiomers).

The term "stereoisomer" refers to isomers of identical constitution that differ in the arrangement of their atoms in space. Enantiomers and diastereomers are stereoisomers wherein an asymmetrically substituted carbon atom acts as a chiral center.

The term "chiral" refers to the structural characteristic of a molecule that makes it impossible to superimpose it on its mirror image.

The term "enantiomer" refers to one of a pair of molecular species that are mirror images of each other and are not superimposable.

The term "diastereomer" refers to stereoisomers that are not mirror images.

The symbols "R" and "S" represent the configuration of substituents around a chiral carbon atom(s).

The term "racemate" or "racemic mixture" refers to a composition composed of equimolar quantities of two enantiomeric species, wherein the composition is devoid of optical activity.

The term "homochiral" refers to a state of enantiomeric purity.

The term "optical activity" refers to the degree to which a homochiral molecule or nonracemic mixture of chiral molecules rotates a plane of polarized light.

The term "geometric isomer" refers to isomers that differ in the orientation of substituent atoms in relationship to a carbon-carbon double bond, to a cycloalkyl ring or to a bridged bicyclic system. Substituent atoms (other than H) on each side of a carbon-carbon double bond may be in an E or Z configuration. In the "E" (opposite sided) configuration, the substituents are on opposite sides in relationship to the carbon-carbon double bond; in the "Z" (same sided) configuration, the substituents are oriented on the same side in relationship to the carbon-carbon double bond. Substituent atoms (other than H) attached to a carbocyclic ring may be in a cis or trans configuration. In the "cis" configuration, the substituents are on the same side in relationship to the plane of the ring; in the "trans" configuration, the substituents are on opposite sides in relationship to the plane of the ring. Compounds having a mixture of "cis" and "trans" species are designated "cis/trans".

It is to be understood that the various substituent stereoisomers, geometric isomers and mixtures thereof used to prepare compounds of the present invention are either commercially available, can be prepared synthetically from commercially available starting materials or can be prepared as isomeric mixtures and then obtained as resolved isomers using techniques well-known to those of ordinary skill in the art.

The isomeric descriptors "R," "S," "E," "Z," "cis," and "trans" are used as described herein for indicating atom configuration(s) relative to a core molecule and are intended to be used as defined in the literature (IUPAC Recommendations for Fundamental Stereochemistry (Section E), *Pure Appl. Chem.*, 1976, 45:13-30).

The compounds of the present invention may be prepared as individual isomers by either isomer-specific synthesis or resolved from an isomeric mixture. Conventional resolution techniques include forming the free base of each isomer of an isomeric pair using an optically active salt (followed by fractional crystallization and regeneration of the free base), forming an ester or amide of each of the isomers of an isomeric pair (followed by chromatographic separation and removal of the chiral auxiliary) or resolving an isomeric mixture of either a starting material or a final product using preparative TLC (thin layer chromatography) or a chiral HPLC (high performance/pressure liquid chromatography) column.

Polymorphs and Solvates

Furthermore, the compound of the present invention may have one or more polymorphic crystalline forms or may be amorphous. As such these forms are intended to be included in the scope of the invention. In addition, the compound may form solvates, for example with water (i.e., hydrates) or common organic solvents (e.g. alcohols). As used herein, the term "solvate" means a physical association of the compound of the present invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. The term "solvate" is intended to encompass both solution-phase and isolatable solvates. Non-limiting examples of suitable solvates include ethanolates, methanolates, and the like. It is intended that the present invention include within its scope solvates of the compound of the present invention. Also the pharmaceutically acceptable salts and N-oxides of the compound of the present invention may form a solvate. Also the solvates of the pharmaceutically acceptable salts and N-oxides of the compound of the invention are included within the scope of the invention.

Thus, in the methods of treatment or prevention of the present invention, the term "administering" shall encompass the means for treating, ameliorating or preventing a syndrome, disorder or disease described herein with the compound of the present invention or a solvate thereof, which would obviously be included within the scope of the invention albeit not specifically disclosed.

Preparation of the Compound of the Present Invention

The compound of formula (I) can be prepared by reductive deuteration of an intermediate of formula (II) wherein $W_1$ represents chloro, bromo or iodo, iodo being preferred, in the presence of deuterium gas and in the presence of a suitable catalyst, such as for example a palladium catalyst, e.g. palladium on charcoal 10% (10% Pd/C), or a Pt catalyst, a palladium catalyst, in particular palladium on charcoal, being preferred, a suitable solvent or solvent mixture, such as for example methanol, deuterated methanol (d1-MeOD, d4-MeOD), tetrahydrofuran, N-methyl-2-pyrrolidone (NMP), or mixtures thereof such as a mixture of tetrahydrofuran and methanol or a mixture of tetrahydrofuran and deuterated methanol, the latter being preferred, and a suitable base, such as for example triethylamine or sodium carbonate ($Na_2CO_3$), the latter being preferred. The catalyst is preferably dried since traces of water can act as an hydrogen source. Additionally, the catalyst is preferably pre-deuterated with deuterium gas to remove catalyst bounded hydrogen. Additionally, the catalyst is preferably washed to remove catalyst bounded hydrogen. The v:v ratio of deuterated methanol to tetrahydrofuran in the solvent mixture is preferably ranging from 1:9 to 1:2, preferably is 1:4.

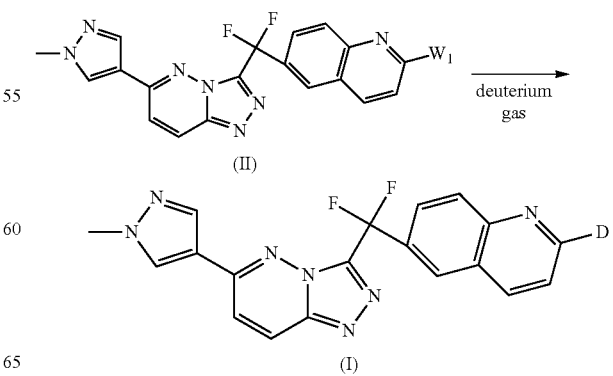

The compound of formula (I) can also be prepared by reacting an intermediate of formula (III) wherein W$_2$ represents a suitable leaving group, such as for example halo, e.g. chloro and the like, with an intermediate of formula (IV) in the presence of a suitable solvent, such as an alcohol, e.g. n-butanol.

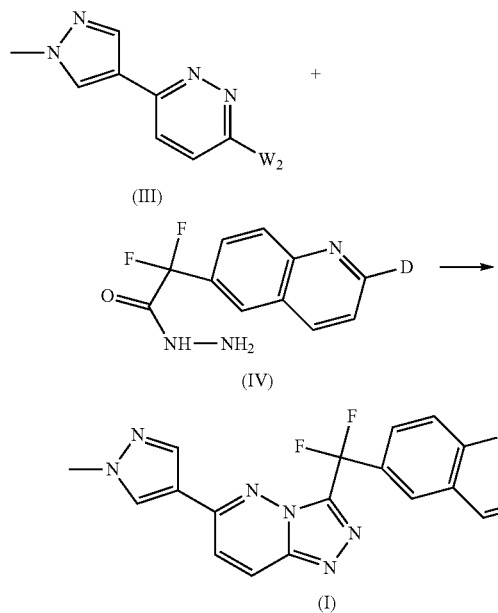

For the synthesis of intermediates of formula (III) reference is made to WO2007/075567, which is incorporated herein by reference.

The compound of formula (I) can also be prepared by reacting an intermediate of formula (V) wherein W$_3$ represents a suitable leaving group, such as for example halo, e.g. chloro and the like, with an intermediate of formula (VI) in the presence of a suitable catalyst, such as for example Pd$_2$dba$_3$, a suitable ligand, such as for example P(tBu$_3$)BF$_4$, a suitable base, such as for example Na$_2$CO$_3$, and a suitable solvent, such as for example dioxane.

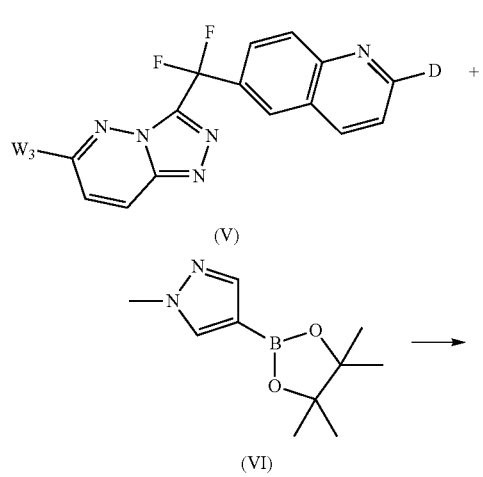

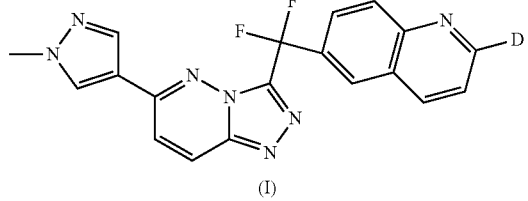

For the synthesis of intermediates of formula (VI) reference is made to WO2007/075567, which is incorporated herein by reference.

Intermediates of formula (V) can be prepared by reacting an intermediate of formula (IV) with an intermediate of formula (VII) wherein W$_3$ is as defined above, in a suitable solvent, such as for example an alcohol, e.g. n-butanol.

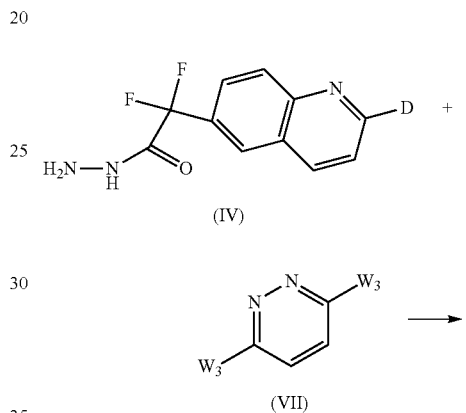

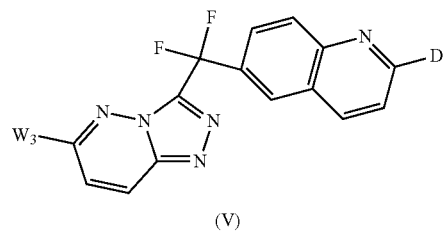

For the synthesis of intermediates of formula (VII) reference is made to WO2007/075567, which is incorporated herein by reference.

An embodiment of the present invention relates to a process of preparing a compound of formula (I) characterized by a) reductive deuteration of an intermediate of formula (II) wherein W$_1$ represents chloro, bromo or iodo in the presence of deuterium gas and in the presence of a suitable catalyst, a suitable solvent or solvent mixture, and a suitable base,

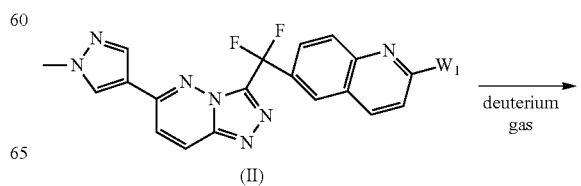

11

-continued

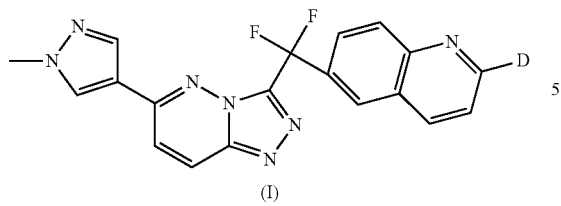

(I)

wherein D represents deuterium;

b) reacting an intermediate of formula (III) wherein $W_2$ represents a suitable leaving group, with an intermediate of formula (IV) wherein D represents deuterium, in the presence of a suitable solvent,

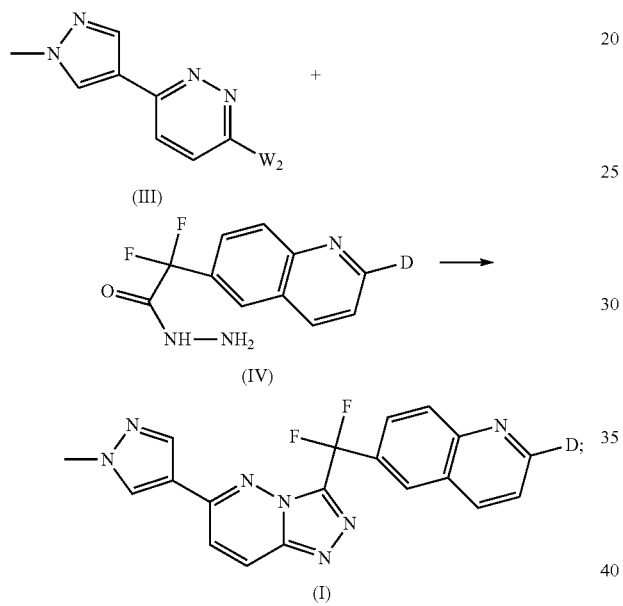

c) reacting an intermediate of formula (V) wherein $W_3$ represents a suitable leaving group and wherein D represents deuterium, with an intermediate of formula (VI) in the presence of a suitable catalyst, a suitable base, and a suitable solvent,

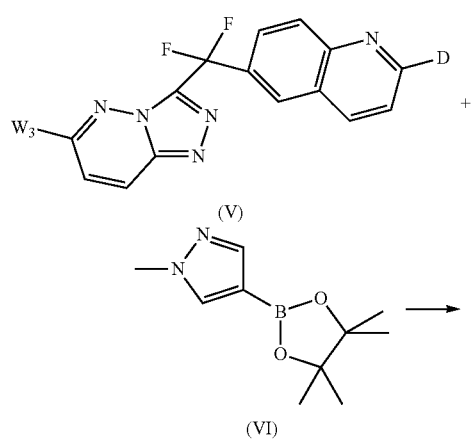

12

-continued

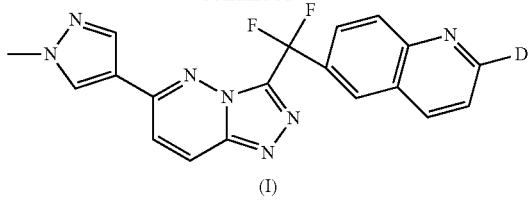

(I)

or, if desired, converting the compound of formula (I), into a therapeutically active non-toxic acid addition salt by treatment with an acid, or conversely, converting the acid addition salt form into the free base by treatment with alkali, or, if desired, preparing, solvates or N-oxide forms thereof.

Examples of individual compound syntheses are shown below.

Example 1

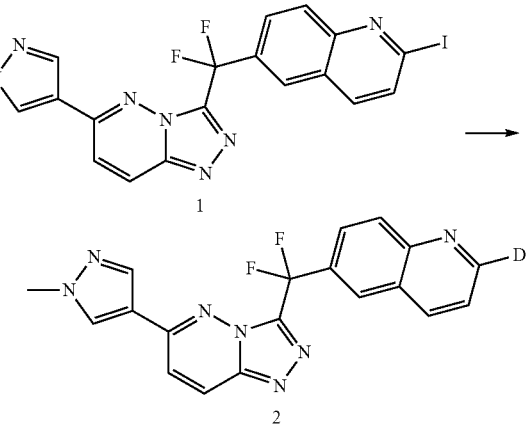

a) Drying the Catalyst:

The catalyst 10% Pd/C (*Escat* 1931, BASF) was dried prior to use. The following conditions were applied
  cabinet drier, applying 85° C./<100 mbar/24 hours followed by applying 85° C./<1 mbar/24 hours
  wet catalyst spread in a beaker glass (filling high<5 mm, container covered with a tissue)

b) Pre-Deuteration of the Catalyst:

A shaked flask (6 L, glass) containing 19.3 g of dry catalyst (10% Pd/C, *Escat* 1931, BASF), 40.6 g sodium carbonate (2 eq., 0.384 mol, Aldrich 71347), 1.6 l tetrahydrofuran (THF) (Aldrich 87371) and 200 ml d1-methanol (Aldrich 151939) was flushed with nitrogen. The shaked flask was sealed, purged with three cycles deuterium/vacuum and finally set under a deuterium atmosphere (1.05 bar, absolute). The shaker was started and the catalyst was pre-deuterated at 25° C. for one hour.

Pre-deuteration was stopped by replacing the deuterium atmosphere with nitrogen. Finally, the solvent was removed by decantation.

c) Reductive Deuteration Procedure:

A slurry of 96.5 g starting material 1 (0.192 mol) in 1.6 l THF (Aldrich 87371) and 390 ml d1-methanol (Aldrich 151939) was added to the pre-deuterated catalyst/additive mixture. The shaked flask was sealed, purged with three cycles deuterium/vacuum and finally set under a deuterium atmosphere (1.05 bar). The shaker was started and the deuterium uptake was monitored. (During the first hour reaction time, the deuterium uptake was on a very low level.)

After 24 hours reaction time, the deuteration was interrupted by replacing the deuterium atmosphere with nitrogen. An analytical sample was taken and analyzed by HPLC. According to HPLC analysis, the starting material was fully converted.

The reaction mixture was diluted with 1l dichloromethane (DCM), the catalyst was filtered off and the filter cake was washed with 500 ml DCM. To isolate the desired product 2, the solvent was removed by evaporation at 45° C./vacuum. Approx. 100 g crude product were isolated as a yellow solid (still containing inorganic salts).

Liquid-Liquid Extraction:

The crude product was taken up in 1.6l DCM/1l1M NaOH and transferred into a separation funnel. After mixing, the two layers were separated and the organic layer was washed with 1l deionised water. All aqueous layers were extracted for a second time with 1l DCM. The two DCM layers were combined, dried over $Na_2SO_4$ and finally the solvent was removed by evaporation (45° C./vacuum).

65.4 g product 2 (compound of formula (I)) were isolated as an off-white solid. According to HPLC analysis, the purity of the material was 97%. Based on $^1$H-NMR analysis, the deuterium content in 2-position of the quinoline moiety was 98.6%

Starting material 1 was prepared according to the below reaction scheme:

Synthesis Starting Material 3

Starting material 4 (400 g) (compound A; WO2007/075567), mCBA (meta-chloroperbenzoic acid) (1.2 eq.) and dichloromethane (10V) (1 V is 1 liter per kg of starting material) were mixed for 17 hours at room temperature. The mixture was neutralized with a saturated aqueous solution of $Na_2CO_3$ until pH>8. The mixture was stirred for 0.5 hour. The mixture was filtered and the solid was washed with water until a pH of about 7. The solid was dried under vacuum at room temperature. Yield: 410 g of starting material 3.

Synthesis Starting Material 2

Starting material 3 (410 g), TosCl (tosyl chloride; 4-methylbenzenesulfonyl chloride) (2 eq.) and dichloromethane (20 V) (1 V is 1 liter per kg of starting material) were mixed. NaOAc (4 eq.) was added and the mixture was stirred for 2 hours. The solvent was removed under vacuum. Methanol was added (20 V). The mixture was stirred. $LiOH.H_2O$ was added (5 eq.) and the mixture was stirred for 17 hours at room temperature. The mixture was concentrated to remove 16 V of methanol and 20 V of water was added. The mixture was neutralized with concentrated HCl until a pH of about 6. The mixture was stirred for 0.5 hour and filtered. The solid was dried under vacuum at 50° C. The solid was slurried with water (10 V) for 0.5 hour. The mixture was filtered. The solid was dried under vacuum at 50° C. The slurrying step and drying step was repeated once. Yield: 375 g of starting material 2.

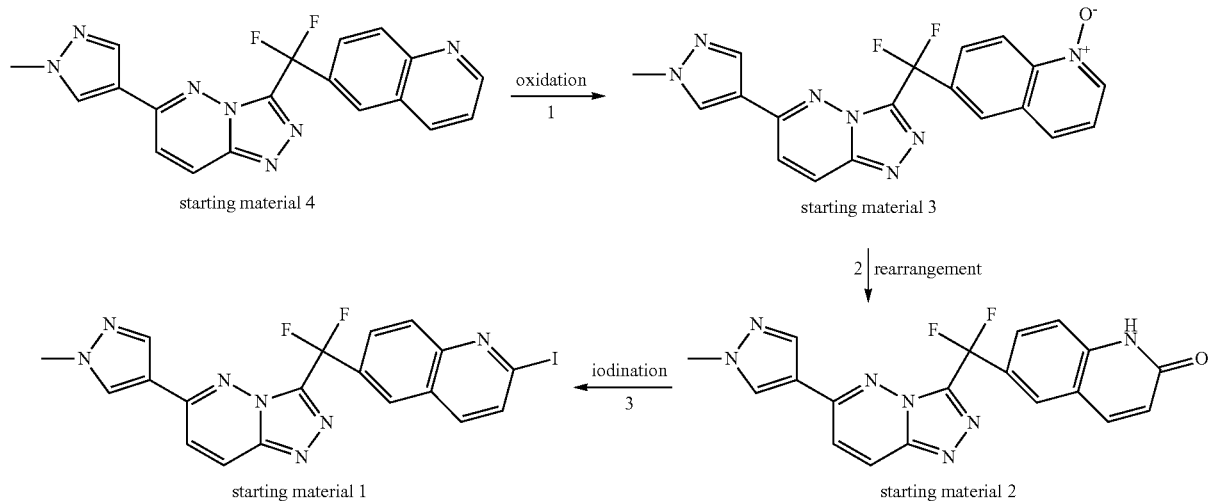

step 1: in the presence of a suitable oxidation reagent, such as for example mCPBA (meta-chloroperbenzoic acid), and a suitable solvent, such as for example dichloromethane. The reaction was performed at room temperature.

step 2: in the presence of TosCl (tosyl chloride; 4-methylbenzenesulfonyl chloride), a suitable base, such as for example NaOAc (sodium acetate), and a suitable solvent, such as for example dichloromethane, followed by reaction in the presence of LiOH, and a suitable solvent, such as for example an alcohol, e.g. methanol.

step 3: in the presence of NaI, $(CF_3SO_2)_2O$ (triflic anhydride; trifluoromethanesulfonic anhydride), in the presence of a suitable solvent, such as for example acetonitrile and pyridine.

Synthesis Starting Material 1

Starting material 2 (190 g), pyridine (1 eq.) and acetonitrile (10 eq.) were mixed and the mixture was cooled down to below 0° C. $(CF_3SO_2)_2O$ (4 eq.) was added slowly dropwise and the reaction temperature was controlled to be no more than 5° C. After addition, the mixture was heated to 20° C. and stirred for 1 hour. The reaction mixture was cooled down to below 0° C. $(CF_3SO_2)_2O$ (1 eq.) was added dropwise. NaI (7 V) (1 V is 1 liter per kg of starting material) was added slowly and the reaction temperature was controlled to be no more than 5° C. After addition, the reaction mixture was heated to 50° C. and stirred for 17 hours at 50° C. Ethyl acetate was added, the mixture was washed with water, 10% $Na_2S_2O_3$ solution, brine. The organic layer was dried with anhydrous $Na_2SO_4$, and purified with gel chromatography. Yield: 98.5 g of starting material 1.

Example 2

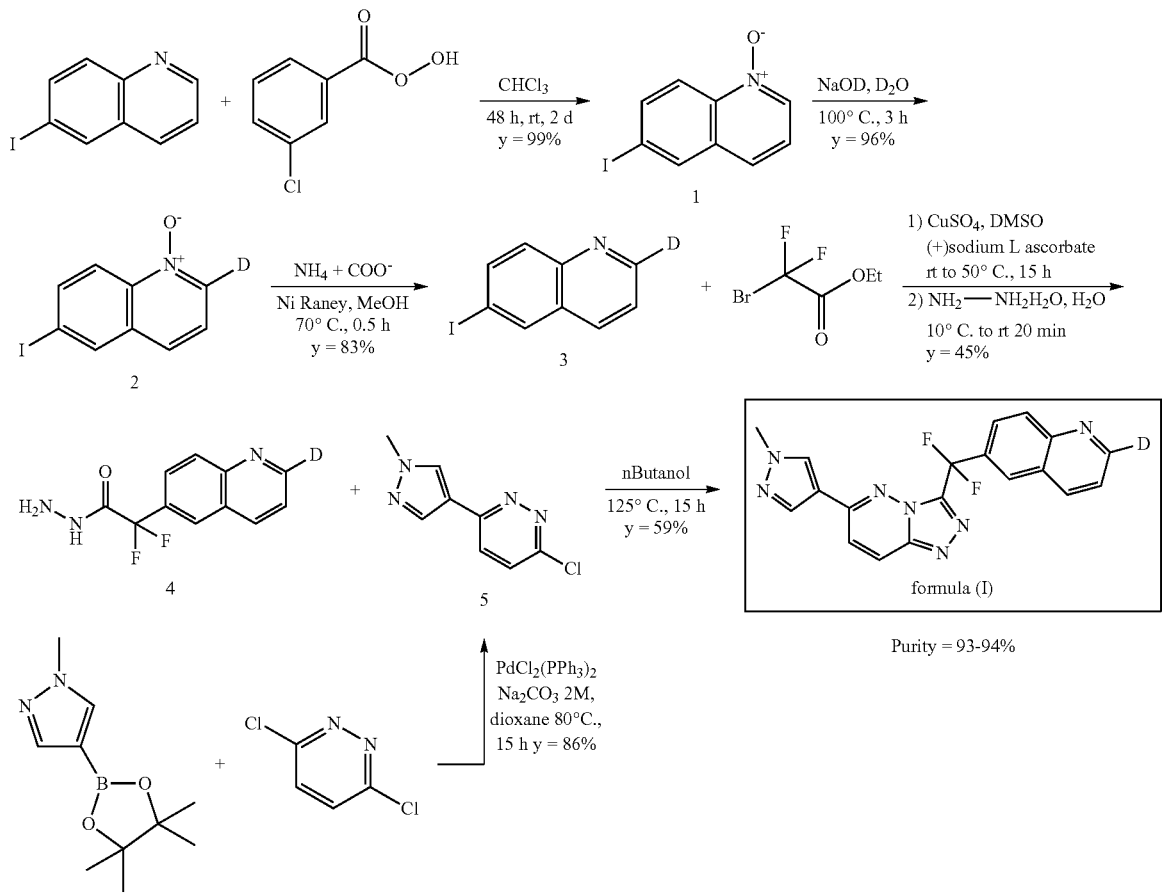

Synthesis of Intermediate 1

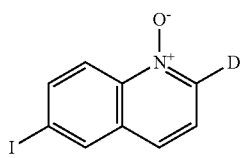 [SMILES: [2H]c1ccc2cc(I)ccc2[n+]1[O-]]

3-chloroperoxybenzoic acid (13.5 g, 78.4 mmol) was added portionwise to 6-iodoquinoline (CAS 13327-31-6) (10 g, 39.2 mmol) in $CHCl_3$ (300 mL) at room temperature. The reaction mixture was stirred for 2 days then poured into an aqueous solution of $K_2CO_3$ 10%. The organic layer was extracted with dichloromethane (DCM). The organic layer was dried ($MgSO_4$), filtered and evaporated until dryness to give 10.5 g of intermediate 1 (99%).

Synthesis of Intermediate 2

A mixture of intermediate 1 (5.2 g, 19.2 mmol) and a solution of NaOD (40% in $D_2O$) (3.4 mL, 48.4 mmol) in $D_2O$ (100 mL) was heated to 100° C. for 2 days. The mixture was cooled to room temperature. $D_2O$ was added and the precipitate was filtered, washed with $D_2O$ and dried to yield 4.9 g of intermediate 2 (96%).

Synthesis of Intermediate 3

A mixture of intermediate 2 (4.8 g, 17.64 mmol), $HCOO-NH_4^+$ (6.68 g, 0.106 mol) and Ni of Raney (6.2 g, 0.106 mol) in MeOH (methanol) (130 mL) were heated to 60° C. for 1.5 hour. The reaction mixture was cooled to room temperature, poured into $D_2O$, basified with $K_2CO_3$ and extracted with EtOAc (ethyl acetate). The organic layer was dried ($MgSO_4$), filtered and evaporated until dryness.

The residue (4 g) was purified by chromatography over silica gel (80 g of irregular SiOH 35-40 μm, mobile phase: graduent from 100% DCM to 95% DCM 5% $CH_3OH$ 0.1% $NH_4OH$). The pure fractions were collected and evaporated until dryness to give 2.9 g of intermediate 3 (83%).

Synthesis of Intermediate 4

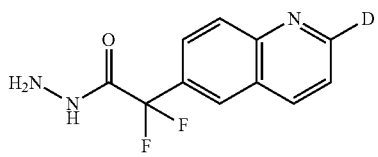 [SMILES: [2H]c1ccc2cc(C(F)(F)C(=O)NN)ccc2n1]

(+)-sodium L-ascorbate (2.32 g, 11.7 mmol) was added to a solution of $CuSO_4.5H_2O$ (1.95 g, 7.8 mmol) in dimethylsulfoxide (DMSO) (25 mL) under $N_2$ at room temperature and the mixture was stirred for 2 hours. Ethylbromodifluoroacetate (0.55 mL, 4.3 mmol) was added and the reaction mixture was stirred for 1.5 hour followed by the addition of intermediate 3 (1 g, 3.9 mmol). After heating at 50° C. for 15 hours, the mixture was cooled down to 10° C. and $NH_2$—$NH_2.H_2O$ (4.76 mL, 78.1 mmol) was added. $H_2O$ (12 mL) was added dropwise (exothermic) and the mixture was stirred at room temperature for 20 minutes. EtOAc was added and the mixture was filtered through a short pad of Celite®. The organic layer was extracted, dried ($MgSO_4$), filtered and evaporated until dryness.

The residue (1 g) was purified by chromatography over silica gel (40 g of silica gel 30 μm, mobile phase: graduent from 100% DCM to 90% DCM 10% $CH_3OH$ 0.1% $NH_4OH$). The pure fractions were collected and evaporated until dryness to give 0.42 g of intermediate 4 (45%).

Synthesis of Intermediate 5

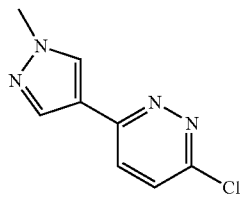

A solution of 3,6-dichloropyridazine (4.57 g, 0.0031 mol), (1-methyl-1H-pyrazol-4-yl)boronic acid pinacol ester (3.82 g, 0.0184 mol) and a solution of $Na_2CO_3$ 2M (18.3 mL) in dioxane (18.4 mL) was stirred for 1 minute. $PdCl_2(PPh_3)_2$ (1.29 g, 0.0018 mol) was added and the solution was heated at 80° C. for 15 hours. The mixture was cooled to room temperature and poured into water. $K_2CO_3$ was added and the mixture was filtered through a short pad of Celite®. The organic layer was dried ($MgSO_4$), filtered and evaporated to dryness. The Celite® was washed with $CH_2Cl_2$, the filtrate was dried ($MgSO_4$) and evaporated. The residue was crystallized from $CH_2Cl_2$. The precipitate was filtered and dried to give 1.5 g of a first batch of intermediate 5 (42%). The filtrate was purified by chromatography over silica gel (30 g of SiOH15-40 μm, mobile phase: gradient from $CH_2Cl_2$ 100% to $CH_2Cl_2$ 95%/$CH_3OH$ 5%). The pure fractions were collected and evaporated until dryness to give 1.58 g of a second batch of intermediate 5 (44%).

Global Yield=86%

Synthesis of Compound of Formula (I)

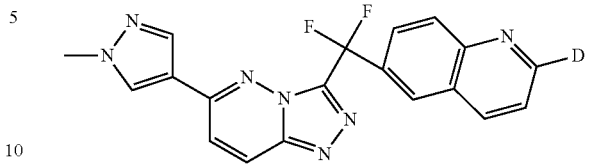

A mixture of intermediate 4 (0.41 g, 1.7 mmol) and intermediate 5 [943541-20-6](0.335 g, 1.7 mmol) in nBu-tanol (30 mL) was heated at 125° C. for 15 hours. The reaction mixture was cooled down to room temperature and evaporated until dryness. The residue was purified by chromatography over silica gel (40 g of irregular SiOH 35-40 μm, mobile phase: graduent from 100% DCM to 90% DCM 10% $CH_3OH$ 0.1% $NH_4OH$). The pure fractions were collected and evaporated until dryness. The residue (0.41 g) was purified by achiral SFC (supercritical fluid chromatography) (Stationary phase: 2 ETHYLPYRIDINE 6 μm 150× 21.2 mm, mobile phase: 85% $CO_2$, 15% MeOH). The pure fractions were collected and evaporated until dryness. The residue (0.387 g) was crystallized from diisopropylether. The precipitate was filtered and dried to give 0.315 g of compound of formula (I) (48%, the deuterium content in 2-position of the quinoline moiety=93-94%). M.P.=201.6° C. (DSC).

Example 3

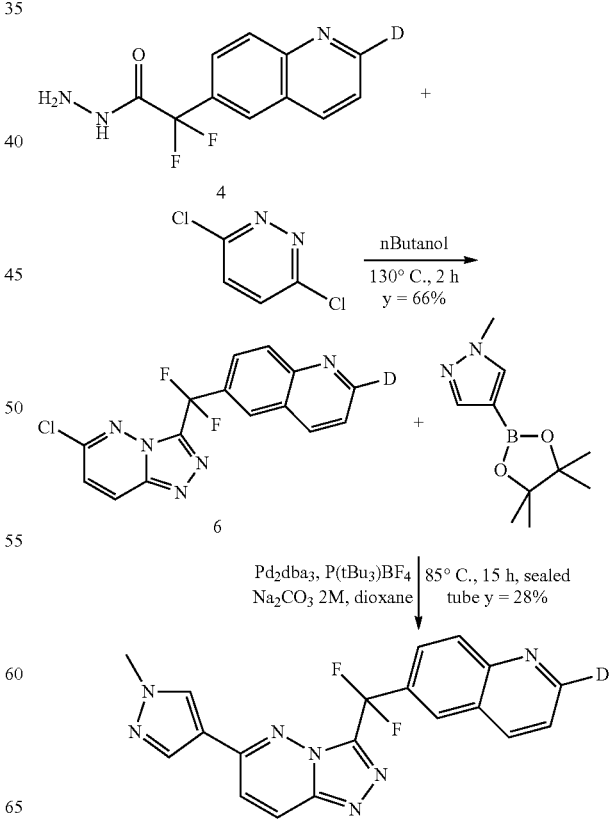

Synthesis of Intermediate 6

A mixture of intermediate 4 (0.42 g, 1.76 mmol) and 3,6-dichloropyridazine (0.788 g, 5.3 mmol) in nButanol (12 mL) was heated at 130° C. for 2 hours. The mixture was cooled down to room temperature and evaporated until dryness. DCM was added and the mixture was stirred with an aqueous solution of $K_2CO_3$ 10%. The organic layer was extracted, dried ($MgSO_4$), filtered and evaporated until dryness. The residue (0.9 g) was purified by chromatography over silica gel (40 g of irregular SiOH 35-40 µm, mobile phase: gradient from 100% DCM to 95% DCM 5% $CH_3OH$ 0.1% $NH_4OH$). The pure fractions were collected and evaporated until dryness to give 0.385 g of intermediate 6 (66%).

Synthesis of Compound of Formula (I)

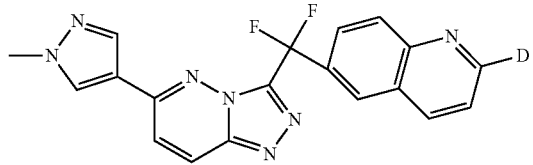 [SMILES: [2H]c1ccc2cc(C(F)(F)c3nnc4ccc(-c5cnn(C)c5)nn34)ccc2n1]

In a sealed tube, a solution of intermediate 6 (183 mg, 0.55 mmol), (1-methyl-1H-pyrazol-4-yl)boronic acid pinacol ester (343 mg, 1.65 mmol), $P(tBu_3)BF_4$ (47.9 mg, 0.165 mmol) and an aqueous solution of $Na_2CO_3$ 2M (1.65 mL, 3.3 mmol) in dioxane (4 mL) was purged with $N_2$ for 10 minutes. $Pd_2dba_3$ (101 mg, 0.11 mmol) was added and the mixture was purged for an additional 5 minutes. The mixture was heated at 85° C. for 15 hours and cooled to room temperature. (1-Methyl-1H-pyrazol-4-yl)boronic acid pinacol ester (343 mg, 1.65 mmol), $P(tBu_3)BF_4$ (47.9 mg, 0.165 mmol), $Pd_2dba_3$ (101 mg, 0.11 mmol) and an aqueous solution of $Na_2CO_3$ 2M (1.65 mL, 3.3 mmol) were added and the mixture was heated at 85° C. for 5 hours. The mixture was cooled down to room temperature, poured into $H_2O+K_2CO_3$ and extracted with EtOAc. The organic layer was dried ($MgSO_4$), filtered and evaporated until dryness. The residue was purified by chromatography over silica gel (24 g of irregular SiOH 35-40 µm, mobile phase: gradient from 100% DCM to 95% DCM 5% $CH_3OH$ 0.1% $NH_4OH$). The pure fractions were collected and evaporated until dryness to give 58 mg of compound of formula (I) (28%, the deuterium content in 2-position of the quinoline moiety was 93-94%).

NMR Method Used to Determine Content of Deuterium/Hydrogen in Example 1

| | |
|---|---|
| Instrument | Bruker Avance 300 |
| Solvent | $CDCl_3$ |
| Sample Preparation | 10-25 mg in 0.7 ml $CDCl_3$, filtered |
| Probe head | 5 mm QNP 1H/13 |
| Pulse program | zg30 |
| Number of Scans | 16 or 254 |
| Temperature | 29° C. |
| Relaxation time | 4.6 sec. |
| Chemical Shifts | According to $^1$H-NMR prediction a chemical shift of 8.84 ppm is expected (ChemOffice). Based on the integral and the expected chemical shift, the hydrogen signal was allocated in the range of 8.9 to 9.0 ppm to the corresponding position. |

NMR Method Used to Determine Content of Deuterium/Hydrogen in Example 2 and 3

| | |
|---|---|
| Instrument | Bruker Avance III 500 |
| Solvent | DMSO or $CDCl_3$ |
| Sample Preparation | ~4 mg in 0.7 ml $CDCl_3$ or DMSO |
| Probe head | 5 mm TXI Z-GRD ($^1$H/$^{13}$C/$^{15}$N) |
| Pulse program | zg30 |
| Number of Scans | 16 |
| Temperature | 22° C. |
| Relaxation time | 1 sec. |
| Chemical Shifts | Deuterium/hydrogen ratio measured based on the integral and chemical shift at 9.02 ppm. |

Analytical HPLC Method for Determination of the Product Purity in Example 1

| | |
|---|---|
| Instruments | Agilent Chemstation 1100 |
| Column | Agilent Eclipse Plus, C18 4.6 × 100 mm, 3.5 um |
| Solvent | A: Water + 0.1% TFA; B: ACN + 0.1% TFA |
| Gradient | 1% B to 100% in 10 min, then 2 min at 100% B; post time: 2 min |
| Flow | 1.0 ml/min. |
| Detection: | UV (220 nm) |
| Temperature | 30° C. |
| Sample concentration | 0.5 mg product in 1.0 ml MeOH |
| Injection volume | 1.0 µL |
| Run time | 14 min. |
| Retention times: | Product 2 (compound of formula (I)): 5.1 minutes. |

Biological Activity

The following representative assays can be performed in determining the biological activities of the compound within the scope of the invention. They are given to illustrate the invention in a non-limiting fashion.

Inhibition of Proliferation of Cancer Cells Carrying Met Amplification and Dependent on Met Signaling by the Compound of Formula (I)

Proliferation Assay with Alamar Blue

Cells were seeded out in a 96-well plate in 180 µl growth medium. Depending on the growth curve test the amount of cells per well was different for each cell line. The cells were incubated overnight in an incubator at 37° C. in a humidified 5% $CO_2$ atmosphere. The next day: The compound plate was prepared and 4 µl of compound was added to 196 µl of pre-warmed medium. 20 µl of this was added to 180 µl of cells. This was incubated for 4 days after adding the compound at 37° C. in a humidified 5% $CO_2$ atmosphere. After the 4 days 40 µl of Alamar blue solution was added. This was incubated at 37° C. in a humidified 5% $CO_2$ atmosphere for 4 hours (depending on the cell line this was tested before at different hours of incubation during the growth curve test). After the 4 hours the fluorescence was measured at excitation 530 nm, emission 590 nm. The fluorescence of control (DMSO treatment) was taken as 100% and the fluorescence of cells incubated with compounds was calculated against the control in %. So a dose response curve could be made and a $IC_{50}$ could be calculated.

Growth Medium, Cell Culture Medium Used:
For Snu-5 Medium

| | |
|---|---|
| IMDM | 500 ml |
| 20% FCS | 120 ml |
| 2 mM L-Glutamine | 6 ml |
| 50 µg/ml Gentamycine | 6 ml |

For EBC-1 Medium

| | |
|---|---|
| EMEM | 500 ml |
| 10% FCS | 57 ml |
| 2 mM L-Glutamine | 5.7 ml |
| 1% PenStrep | 5.7 ml |

Results:

| Cell line | IC$_{50}$ compound A [M] | IC$_{50}$ compound of formula (I) [M] |
|---|---|---|
| SNU-5 | 1.38E−8 | 1.32E−8 |
| EBC1 | 1.34E−08 | 1.2E−08 |

Inhibition of Phosphorylation of Met in Dose Response by Compound of Formula (I)
Western Blot
Cell line: EBC-1 and Sun-5

Samples were run on SDS-PAGE. After that the gel was run on an I-Blot machine (Invitrogen). Principle: by electrical the proteins were transferred to the PDVF membrane.

The PDVF membrane was first blocked for 1 hour at room temperature with blocking buffer (Odyssey Blocking buffer (PBS); Licor). After blocking the membrane was incubated with the primary antibody for overnight at 4° C. The next day the blots were washed with TBS-tween 0.1% 3 times 5 minutes. The secondary antibody was put onto the blot for 1 hour at room temperature. After incubation the blots were washed with TBS-tween 0.1% for 3 times 5 minutes. The blots were scanned for signal.

Antibodies Used:
Primary Antibodies:
  Cell Signaling technology #3077, anti-pMet (Tyr1234/1235) rabbit mAb, 1/2,000
  Cell Signaling technology #3127, anti-Met (25H2) mouse mAb, 1/1,000
  Sigma A1978, anti-b-Act mouse mAb, 1/30,000
Secondary Antibodies:
  Invitrogen #A21076, Alexa Fluor® 680 Goat Anti-Rabbit IgG (H+L), 1/4,000
  Rockland #610-732-124, Mouse IgG (H&L) Antibody IRDye800® Conjugated Pre-adsorbed, 1/4,000

Results are Shown in FIGS. 1A-1D

In Vivo Pharmacokinetic Determination of Compound (I), Compound A and their Metabolites in New Zealand White Rabbits.

Male New Zealand rabbits (Crl: KBL (NZW), Charles River, France) and female New Zealand rabbits (NZW INRA A1077, Centre Lago) were used. Per compound (compound of formula (I) and compound A) one male and two female rabbits were used with a mean weight of 2.6±0.2 kg. A complete plasma concentration time-profile was obtained from each individual animal. Standard diet and tap water were available ad libitum. Compound of formula (I) and compound A were both dissolved in a 10% (w/v) SBE-B-CD (sulfobutyl ether-beta-cyclodextrin) research grade (Captisol) solution at a final concentration of 1 mg/ml. HCl and PVP K30 were added to facilitate dissolution of the compounds. After total dissolution, the pH was brought up to 2.6/2.7 with NaOH. The formulations were stored at room temperature, protected from light and analysed quantitatively with LC-MS/MS on the day of preparation. Stability of the formulations was checked on the day of dosing. Animals were dosed orally by gavage at 10 ml/kg to obtain a final dose of 10 mg/kg. From each individual dosed animal, blood samples were taken at 30 minutes, 1, 2, 4, 7 and 24 hours after oral administration. Blood was collected by multiple sampling from a lateral ear vein into Multivette® 600 K3E tubes (Sarstedt). Samples were placed immediately on melting ice and plasma was obtained following centrifugation at 4° C. for 10 minutes at approximately 1900×g. All samples were shielded from daylight and stored at ≤−18° C. prior to analysis. Plasma samples were analysed for compound (I), compound A, metabolite 1, metabolite 2, N-desmethyl metabolite 3 (which was calculated on the curve of N-desmethyl metabolite 4) and N-desmethyl metabolite 4 using a qualified research LC-MS/MS method. The key analytical performance (linearity, upper and lower limit of quantification, accuracy and precision) of the method was reported together with the plasma concentrations. The lower limit of quantification (LLOQ) for plasma was 1.00 ng/ml for all compounds. A limited pharmacokinetic analysis was performed using Phoenix™ Professional (Version 6.2.1). A non-compartmental analysis using the lin/log trapezoidal rule with lin/log interpolation was used for all data.

Results

Basic pharmacokinetic parameters of compound of formula (I) and its metabolites after single oral administration at 10 mg/kg of compound (I) in male and female rabbit. Compound A was also detected (impurity)

| | Compound of formula (I) | Compound A | Metabolite 1 | Metabolite 2 | N-desmethyl metabolite 3 |
|---|---|---|---|---|---|
| Cmax (ng/ml) | 3570 ± 2316 | 27.6 ± 17.4 | 57.5 ± 34.2 | 39.8 ± 13.1 | 738 ± 447 |
| Tmax (h) | 0.5 ± 0.0 | 0.5 ± 0.0 | 2.3 ± 1.5 | 0.8 ± 0.3 | 1.2 ± 0.8 |
| T½ (h) | ND* | 2.1 ± 0.4 | ND | ND | 4.4 ± 1.9 |
| AUC0-last (ng · h/ml) | 8460 ± 6519 | 53.7 ± 40.6 | ND | 127 ± 65 | 2308 ± 392 |
| AUC0-inf (ng · h/ml) | 8567 ± 6437 | 62.3 ± 47.8 | 409 ± 7.0 | 152 ± 81 | 2356 ± 450 |
| MRT** (h) | 4.6 ± 1.0 | 3.24 ± 0.76 | 7.0 ± 0.7 | 3.8 ± 0.7 | 5.1 ± 0.3 |

*ND: not determined

**MRT: mean residence time (hours)

Basic pharmacokinetic parameters of compound A and its metabolites after single oral administration at 10 mg/kg of compound A in male and female rabbit.

|  | Compound A | Metabolite 1 | Metabolite 2 | N-desmethyl metabolite 4 |
|---|---|---|---|---|
| Cmax (ng/ml) | 1830 ± 1361 | 126 ± 80 | 84.4 ± 55.9 | 299 ± 146 |
| Tmax (h) | 1.0 ± 0.0 | 2.7 ± 1.2 | 1.0 ± 0.0 | 1.3 ± 0.6 |
| T½ (h) | ND* | ND | 3.0 ± 0.5 | ND |
| AUC0-last (ng · h/ml) | 8187 ± 5735 | 934 ± 336 | 341 ± 259 | 1494 ± 193 |
| AUC0-inf (ng · h/ml) | 8222 ± 5738 | 1054 ± 421 | 439 ± 331 | 1507 ± 190 |
| MRT (h)** | 5.2 ± 0.9 | 7.8 ± 1.4 | 5.0 ± 09 | 5.7 ± 0.9 |

*ND: not determined
**MRT: mean residence time (hours)

Metabolite 1:

6-{Difluoro[6-(1H-pyrazol-4-yl)[1,2,4]triazolo[4,3-b]pyridazin-3-yl]methyl}quinolin-2(1H)-one Metabolite 2:

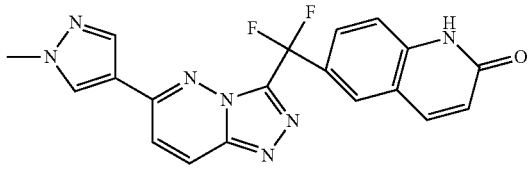 [SMILES: Cn1cc(-c2ccc3nnc(C(F)(F)c4ccc5[nH]c(=O)ccc5c4)n3n2)cn1]

6-{Difluoro[6-(1-methyl-1H-pyrazol-4-yl)[1,2,4]triazolo[4,3-b]pyridazin-3-yl]methyl}quinolin-2(1H)-one N-desmethyl metabolite 3;

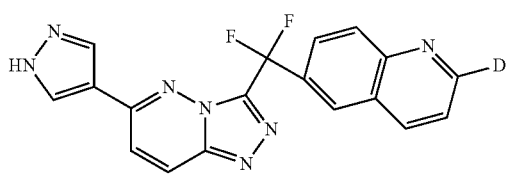 [SMILES: [2H]c1ccc2cc(C(F)(F)c3nnc4ccc(-c5cn[nH]c5)nn34)ccc2n1]

N-desmethyl metabolite 4;

6-{Difluoro[6-(1H-pyrazol-4-yl)[1,2,4]triazolo[4,3-b]pyridazin-3-yl]methyl}quinoline An In Vitro Study on the Inhibition of OCT2 (SLC22A2) Transport by the Compound of Formula (I)

This was tested using Chinese Hamster Ovary (CHO) cells, parental or stably transfected with OCT2. $^{14}$C-Metformin was used as OCT2 substrate.

CHO cell lines, parental and stably transfected with OCT2 were obtained from Solvo Biotechnology (Hungary).

CHO cells were cultured in DMEM-F12 (Dulbecco's Modified Eagle Medium) supplemented with 0.03 mg/mL L-Proline, 1% L-Glutamine, penicillin (50-100 U/mL), streptomycin (50-100 μg/mL) and 10% (v/v) foetal calf or bovine serum (FCS) further referred to as "CHO culture medium".

1. OCT2 Inhibition Test

Compound Formulations

If needed, non-radiolabeled and radio-labeled compounds were mixed to obtain the proper chemical and radioactive concentration. Stock solutions (200×) were prepared using the solvent indicated in the Table below. Proper solvent controls were included. The test items and all reference and inhibitory compounds required are mentioned in Table below.

For parental and OCT2 transfected CHO cell lines:

| Substrates | | | | Inhibitors | | | | Incubation | |
|---|---|---|---|---|---|---|---|---|---|
| Identity | Solvent | Fold dilution | Final conc. | Identity | Solvent | Fold dilution | Final conc.(s) | time (min) | Cell lines |
| $^{14}$C-metformin | HBSS$^{+/+}$ + 10 mM Hepes (pH 7.4) | 1x | 10 μM (10 kBq/mL) | Quinidine | DMSO | 200x | 0, 300 μM | 1 | Parent & OCT2 |
|  |  |  |  | Compound of formula (I) | DMSO | 200x | 0, 0.3, 1, 3, 10, 30, 100 μM | 1 | Parent & OCT2 |

Incubation Procedure

T=−24 Hours

Both, CHO parental and OCT2 cells were seeded into 24 well plates (1 mL/well, 400 000 cells/well) in CHO culture medium.

Day of the Experiment

Transport experiments were performed in Hank's Balanced Salt Solution$^{+Ca,+Mg}$(HBSS$^{+/+}$) supplemented with 10 mM HEPES at pH 7.4. All media added to the cells and plates were kept at 37° C.

Before the incubation, the cells in each well were washed twice with 1 mL HBSS$^{+/+}$+10 mM Hepes pH 7.4 at 37° C. Next, the incubation medium, containing reference substrate and the inhibitors (or inhibitor solvent) was added (250 μL/well).

At the time of dose administration (0 min), 150 μL of the dosing solution was sampled in triplicate for determination of initial concentrations by Liquid Scintillation Counting (LSC). During the incubation period, the plates were kept at 37° C.

To stop the reaction, 1.5 mL ice-cold HBSS$^{+/+}$ was added to each well and the liquids were aspirated. Again, to each well 2 mL ice-cold HBSS$^{+/+}$ was added and aspirated while keeping the plate angled. Following aspiration of the last well, all the wells were aspirated again taking care of not touching the cells.

To lyse the cells, 250 μL of Mammalian Protein Extraction Reagent (M-PER) lysis buffer was added to each well and the plates were shaken for at least 10 minutes (400 rpm). For LSC, a 150 μL sample/well was taken and for protein analysis a 25 μL sample/well. Protein analysis was carried out according to the bicinchoninic acid (BCA) method.

Data Analysis

The data is expressed in picomoles per mg protein per minute and as percentage of control (solvent control=DMSO). Sigmaplot was used to calculate IC$_{50}$ values.

Results and Discussion

The uptake of $^{14}$C-Metformin (OCT2 substrate) was much higher (7.39 and 17.2 fold) in the OCT2 transfected CHO cells compared to the parental cells. This uptake was inhibited by the positive control inhibitor, 300 μM quinidine (85.5% and 100%). These data indicate that the assay conditions used, worked efficiently to study the inhibitory effect of the test compound on OCT2 dependent transport.

The compound of formula (I) showed inhibition of $^{14}$C-Metformin uptake in OCT2 cells with an IC$_{50}$ of 0.67±0.02 μM.

Cytotoxicity Test

Cytotoxicity of the compound of formula (I) was determined at 100 μM, and this in both CHO parental and OCT2 cells. Also a 1% Triton-X100 condition was included, as a positive control cytotoxic reagent. After 1 minute of incubation the supernatant was aspirated, the dry cells washed twice with 1 mL HBSS$^{+/+}$+10 mM Hepes pH 7.4 (37° C.). After aspiration of the buffer, a 1/10 dilution of the PrestoBlue™ Viability Reagent (Life Technologies) in HBSS$^{+/+}$+10 mM Hepes pH 7.4 was added and plates were incubated for 60 minutes at 37° C., protected from light. Each well was sampled (150 μL) in a black 96-well plate and fluorescence was measured (Excitation: 560 nm/12 nm bandwith, Emission: 590 nm/12 nm bandwith).

Results and Discussion

For the compound of formula (I) at 100 μM no cytotoxic effects were observed. With the positive control cytotoxic reagent, a 1% solution of Triton X-100, viability dropped dramatically (see below Table). This indicates that possible inhibitory effects are not related to a loss of cell viability.

| Condition | Cell Viability (%) (after 1 minute of incubation) | |
| --- | --- | --- |
| | in CHO Parental cells | in CHO OCT2 cells |
| (DMSO control) | 100 | 100 |
| Compound of formula (I) 100 μM | 104 | 103 |
| Triton X-100 1% | 0 | 0 |

Methods of Treatment/Prevention; Use of the Compound

In another aspect of the invention, the compound of the invention can be used to inhibit tyrosine kinase activity or expression, including c-Met activity, reduce kinase activity or expression, including c-Met activity, and modulate expression of c-Met in a cell or a subject, or to treat disorders related to c-Met kinase activity or expression in a subject. Inhibition of c-Met activity is believed to indirectly modulate c-Met expression.

In one embodiment to this aspect, the present invention provides a method for reducing or inhibiting the kinase activity of c-Met, and modulate expression of c-Met in a cell comprising the step of contacting the cell with a compound of formula (I). The present invention also provides a method for reducing or inhibiting the kinase activity of c-Met, and modulate expression of c-Met in a subject comprising the step of administering a compound of formula (I) to the subject. The present invention further provides a method of inhibiting cell proliferation in a cell comprising the step of contacting the cell with a compound of formula (I). The present invention further provides for the compound of formula (I) for reducing or inhibiting the kinase activity of c-Met, and modulate expression of c-Met.

The term "subject" as used herein, refers to an animal, preferably a mammal, most preferably a human, who has been the object of treatment, observation or experiment.

The term "contacting" as used herein, refers to the addition of compound to cells such that compound is taken up by the cell.

In other embodiments to this aspect, the present invention provides both prophylactic and therapeutic methods for treating a subject at risk of (or susceptible to) developing a cell proliferative disorder or a disorder related to c-Met. Such disorders include pre-existing conditions related to c-Met expression (or over expression) and/or c-Met mutation.

In one example, the invention provides methods for preventing in a subject a cell proliferative disorder or a disorder related to c-Met, comprising administering to the subject a prophylactically effective amount of a pharmaceutical composition comprising the compound of formula (I) and a pharmaceutically acceptable carrier. Administration of said prophylactic agent can occur prior to the manifestation of symptoms characteristic of the cell proliferative disorder or disorder related to c-Met, such that a disease or disorder is prevented or, alternatively, delayed in its progression. The invention provides for the compound of formula (I) for use in preventing a cell proliferative disorder or a disorder related to c-Met. The invention provides for the use of the compound of formula (I) for the manufacture of a medicament for preventing a cell proliferative disorder or a disorder related to c-Met.

In another example, the invention pertains to methods of treating in a subject a cell proliferative disorder or a disorder related to c-Met comprising administering to the subject a therapeutically effective amount of a pharmaceutical composition comprising the compound of formula (I) and a pharmaceutically acceptable carrier. Administration of said therapeutic agent can occur concurrently with the manifestation of symptoms characteristic of the disorder, such that said therapeutic agent serves as a therapy to compensate for the cell proliferative disorder or disorders related to c-Met. The invention provides for the compound of formula (I) for use in the treatment of a cell proliferative disorder or a disorder related to c-Met. The invention provides for the use of the compound of formula (I) for the manufacture of a medicament for the treatment of a cell proliferative disorder or a disorder related to c-Met.

In another example, the invention pertains to methods of modulating in a subject a cell proliferative disorder or a disorder related to c-Met, such that modulation of the level of c-Met expression or of c-Met activity may act to ameliorate the cell proliferative disorder or a disorder related to c-Met, comprising administering to the subject a therapeutically effective amount of a pharmaceutical composition comprising the compound of formula (I) and a pharmaceutically acceptable carrier. The invention provides for the compound of formula (I) for use in modulating a cell proliferative disorder or a disorder related to c-Met, such that modulation of the level of c-Met expression or of c-Met activity may act to ameliorate the cell proliferative disorder or a disorder related to c-Met. The invention provides for the use of a compound of formula (I) for the manufacture of a medicament for modulating a cell proliferative disorder or a disorder related to c-Met, such that modulation of the level of c-Met expression or of c-Met activity may act to ameliorate the cell proliferative disorder or a disorder related to c-Met.

The term "prophylactically effective amount" refers to an amount of an active compound or pharmaceutical agent that inhibits or delays in a subject the onset of a disorder as being sought by a researcher, veterinarian, medical doctor or other clinician.

The term "therapeutically effective amount" as used herein, refers to an amount of active compound or pharmaceutical agent that elicits the biological or medicinal response in a subject that is being sought by a researcher, veterinarian, medical doctor or other clinician, which includes alleviation of the symptoms of the disease or disorder being treated.

Methods are known in the art for determining therapeutically and prophylactically effective doses for the instant pharmaceutical composition.

Methods are known in the art for determining therapeutically and prophylactically effective amounts for the instant compounds.

As used herein, the term "composition" is intended to encompass a product comprising the specified ingredients in the specified amounts, as well as any product which results, directly or indirectly, from combinations of the specified ingredients in the specified amounts.

As used herein, the terms "disorders related to c-Met", or "disorders related to c-Met receptor tyrosine kinase" shall include diseases associated with or implicating c-Met activity, for example, the overactivity of c-Met, and conditions that accompany with these diseases. The term "overactivity of c-Met" refers to either 1) c-Met expression in cells which normally do not express c-Met; 2) c-Met activity by cells which normally do not possess active c-Met; 3) increased c-Met expression leading to unwanted cell proliferation; or 4) mutations leading to constitutive activation of c-Met. Examples of "disorders related to c-Met" include disorders resulting from over stimulation of c-Met due to abnormally high amount of c-Met or mutations in c-Met, or disorders resulting from abnormally high amount of c-Met activity due to abnormally high amount of c-Met or mutations in c-Met.

It is known that overactivity of c-Met has been implicated in the pathogenesis of a number of diseases, such as cell proliferative disorders, neoplastic disorders and cancers.

The term "cell proliferative disorders" refers to unwanted cell proliferation of one or more subset of cells in a multicellular organism resulting in harm (i.e., discomfort or decreased life expectancy) to the multicellular organisms. Cell proliferative disorders can occur in different types of animals and humans. Cell proliferative disorders include neoplastic disorders (as used herein, a "neoplastic disorder" refers to a tumor resulting from abnormal or uncontrolled cellular growth) and other cell proliferative disorders.

Examples of cell proliferative disorders related to c-Met, include tumors and cancers—for instance, hereditary and sporadic human papillary renal carcinomas, breast cancer, colorectal cancer, gastric carcinoma, glioma, ovarian cancer, hepatocellular carcinoma, head and neck squamous cell carcinomas, testicular carcinoma, basal cell carcinoma, liver carcinoma, sarcoma, malignant pleural mesothelioma, melanoma, multiple myeloma, osteosarcoma, pancreatic cancer, prostate cancer, synovial sarcoma, thyroid carcinoma, non-small cell lung cancer (NSCLC) and small cell lung cancer, transitional cell carcinoma of urinary bladder, testicular carcinoma, basal cell carcinoma, liver carcinoma—including leukemias, lymphomas, and myelomas—for instance, acute lymphocytic leukemia (ALL), acute myeloid leukemia (AML), acute promyelocytic leukemia (APL), chronic lymphocytic leukemia (CLL), chronic myeloid leukemia (CML), chronic neutrophilic leukemia (CNL), acute undifferentiated leukemia (AUL), anaplastic large-cell lymphoma (ALCL), prolymphocytic leukemia (PML), juvenile myelomonocytic leukemia (JMML), adult T-cell ALL, AML with trilineage myelodysplasia (AML/TMDS), mixed lineage leukemia (MLL), myelodysplastic syndromes (MDSs), myeloproliferative disorders (MPD), multiple myeloma, (MM), myeloid sarcoma, non-Hodgkin's lymphoma and Hodgkin's disease (also called Hodgkin's lymphoma)—and diseases associated with the formation of new vasculature, such as rheumatoid, arthritis, and retinopathy.

Other cell proliferative disorders in which overactivity of c-Met has been implicated in their pathogenesis include cancers in which c-Met activity contributes to the invasive/metastatic phenotype, including cancers in which c-Met is not overexpressed or otherwise altered.

In a further embodiment to this aspect, the invention encompasses a combination therapy for treating or inhibiting the onset of a cell proliferative disorder or a disorder related to c-Met in a subject. The combination therapy comprises administering to the subject a therapeutically or prophylactically effective amount of a compound of formula (I), and one or more other anti-cell proliferation therapy including chemotherapy, radiation therapy, gene therapy and immunotherapy.

In an embodiment of the present invention, the compound of the present invention may be administered in combination with chemotherapy. As used herein, chemotherapy refers to a therapy involving a chemotherapeutic agent. Thus, the present invention relates to a combination of a compound of formula (I) and another chemotherapeutic agent. A variety of chemotherapeutic agents may be used in the combined treatment methods disclosed herein. Chemotherapeutic agents contemplated as exemplary, include, but are not limited to: platinum compounds (platinum containing anticancer drug) (e.g., cisplatin, carboplatin, oxaliplatin); taxane compounds (e.g., paclitaxcel, docetaxol); campotothecin compounds (irinotecan, topotecan); vinca alkaloids (e.g., vincristine, vinblastine, vinorelbine); anti-tumor nucleoside derivatives (e.g., 5-fluorouracil, leucovorin, gemcitabine, capecitabine); alkylating agents (e.g., cyclophosphamide, carmustine, lomustine, thiotepa); epipodophyllotoxins/podophyllotoxins (e.g. etoposide, teniposide); aromatase inhibitors (e.g., anastrozole, letrozole, exemestane); anti-estrogen compounds (e.g., tamoxifen, fulvestrant), antifolates (e.g., premetrexed disodium); hypomethylating agents (e.g., azacitidine); biologics (e.g., gemtuzamab, cetuximab, rituximab, pertuzumab, trastuzumab, bevacizumab, erlotinib); antibiotics/anthracylines (e.g. idarubicin, actinomycin D, bleomycin, daunorubicin, doxorubicin, mitomycin C, dactinomycin, carminomycin, daunomycin); antimetabolites (e.g., clofarabine, aminopterin, cytosine arabinoside, methotrexate); tubulin-binding agents (e.g. combretastatin, colchicine, nocodazole); topoisomerase inhibitors (e.g., camptothecin); differentiating agents (e.g., retinoids, vitamin D and retinoic acid); retinoic acid metabolism blocking agents (RAMBA) (e.g., accutane); kinase inhibitors (e.g., flavoperidol, imatinib mesylate, gefitinib); famesyltransferase inhibitors (e.g., tipifarnib); histone deacetylase inhibitors; inhibitors of the ubiquitin-proteasome pathway (e.g., bortezomib, Yondelis); FGFR (fibroblast growth factor receptor) inhibitors.

In an embodiment, chemotherapeutic agents that may in particular be used in combinations as described herein are platinum compounds (platinum containing anti-cancer drugs) (e.g. cisplatin, carboplatin, oxaliplatin) in particular in view of the OCT2 inhibiting activity of the compound of formula (I). This combination may reduce the side effects of the platinum compounds and hence may provide for a longer treatment period with the platinum compounds. Thus, the invention relates to a combination of a compound of formula (I) and a platinum containing anti-cancer drug, such as for example cisplatin, carboplatin, oxaliplatin. In an aspect, the present invention relates to a product containing as first active ingredient a platinum containing anti-cancer drug, such as for example cisplatin, carboplatin, oxaliplatin, and as second active ingredient a compound of formula (I), as a combined preparation for simultaneous, separate or sequential use in the treatment of patients suffering from cancer.

In the combinations of the present invention, the platinum containing anti-cancer drug, such as for example cisplatin, carboplatin, oxaliplatin, and the compound of formula (I) may be formulated in separate pharmaceutical dosage forms, that can be sold independently from each other, but with the indication or instruction for their combined use. Said indication or instruction can be in the form of a patient leaflet or the like, or in the form of any communication, for instance in written or oral form.

In an embodiment, chemotherapeutic agents that may in particular be used in combinations as described herein are FGFR inhibitors. These combinations may be of particular interest in that the cMet inhibitor of formula (I) can be used to prevent resistance, delay resistance, prevent emergence of resistance or delay the emergence of resistance of a tumour or a cancer to a FGFR inhibitor, in particular a FGFR inhibitor as described herein.

In an aspect, the present invention relates to a product containing as first active ingredient a FGFR inhibitor, and as second active ingredient a compound of formula (I), as a combined preparation for simultaneous, separate or sequential use in the treatment of patients suffering from cancer.

The FGFR inhibitor and the compound of formula (I) may be administered simultaneously (e.g. in separate or unitary compositions) or sequentially in either order. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular other medicinal agent and compounds of the combinations of the present invention being administered, their route of administration, the particular tumour being treated and the particular host being treated. The optimum method and order of administration and the dosage amounts and regime can be readily determined by those skilled in the art using conventional methods and in view of the information set out herein.

The weight ratio of the compounds of the combinations may be determined by the person skilled in the art. Said ratio and the exact dosage and frequency of administration depends on the particular compounds of the combinations, the particular condition being treated, the severity of the condition being treated, the age, weight, gender, diet, time of administration and general physical condition of the particular patient, the mode of administration as well as other medication the individual may be taking, as is well known to those skilled in the art. Furthermore, it is evident that the effective daily amount may be lowered or increased depending on the response of the treated subject and/or depending on the evaluation of the physician prescribing the combinations of the instant invention. The weight-by-weight ratio for the FGFR inhibitor and the compound of formula (I) may range from 1/10 to 10/1, more in particular from 1/5 to 5/1, even more in particular from 1/3 to 3/1.

In one embodiment, the FGFR inhibitor and the compound of formula (I) of the combinations of the present invention are administered sequentially in either order, on separate dosing schedules. In this case, the two compounds will be administered within a period and in an amount and manner that is sufficient to ensure that an advantageous or synergistic effect is achieved.

In the combinations of the present invention, the FGFR inhibitor and the compound of formula (I) may be formulated in separate pharmaceutical dosage forms, that can be sold independently from each other, but with the indication or instruction for their combined use. Said indication or instruction can be in the form of a patient leaflet or the like, or in the form of any communication, for instance in written or oral form.

In the combinations of the present invention, the FGFR inhibitor and the compound of formula (I) can be administered via the same route of administration or via different routes of administration.

In one embodiment, the FGFR inhibitor and the compound of formula (I) of the combinations of the present invention are administered via the same route of administration, in particular via oral route.

The present invention also relates to a pharmaceutical product or a commercial package comprising a combination according to the present invention, in particular together with instructions for simultaneous, separate or sequential use in the treatment of an FGFR tyrosine kinase activity mediated disease, especially a cancer.

In one embodiment, in the combinations of the present invention, the FGFR inhibitor and the compound of formula (I) are administered simultaneously.

In case of a combination of the present invention comprising compound X or a pharmaceutically acceptable salt thereof or a solvate thereof as the FGFR inhibitor it may be advantageous to administer said compound less frequent than the compound of formula (I) because compound X shows lysosomotropic properties and prolonged target shut down.

The FGFR inhibitor and the compound of formula (I) of the combinations of the present invention may also be co-formulated in a single formulation.

In one embodiment, the present invention relates to a pharmaceutical composition comprising a pharmaceutically acceptable carrier and as a first active ingredient a FGFR inhibitor, in particular a compound selected from N-(3,5- dimethoxyphenyl)-N'-(1-methylethyl)-N-[3-(1-methyl-1H-pyrazol-4-yl)quinoxalin-6-yl]ethane-1,2-diamine or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine or a pharmaceutically acceptable salt thereof or a solvate thereof; and as a second active ingredient the compound of formula (I).

Examples of FGFR Inhibitors

*) N-(3,5-dimethoxyphenyl)-N'-(1-methylethyl)-N-[3-(1-methyl-1H-pyrazol-4-yl)quinoxalin-6-yl]ethane-1,2-diamine (compound X) is represented by the following formula compound X

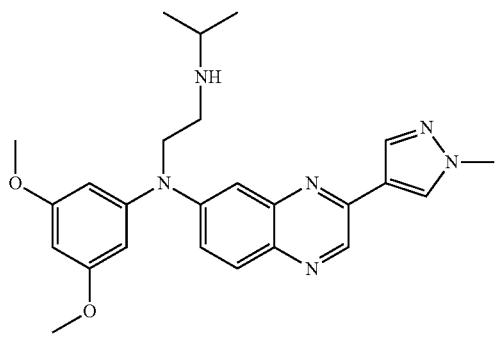

*) N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine (compound Y) is represented by the following formula compound Y

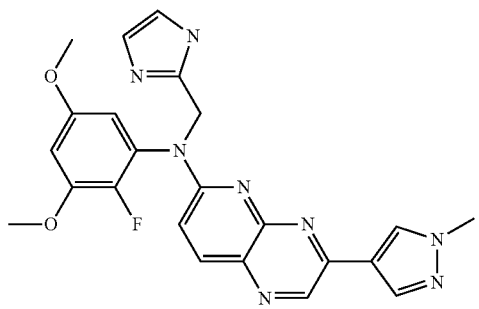

Compounds N-(3,5-dimethoxyphenyl)-N'-(1-methylethyl)-N-[3-(1-methyl-1H-pyrazol-4-yl)quinoxalin-6-yl]ethane-1,2-diamine (compound X) or a pharmaceutically acceptable salt thereof or a solvate thereof, and N-(2-fluoro-3,5-dimethoxyphenyl)-N-(1H-imidazol-2-ylmethyl)-3-(1-methyl-1H-pyrazol-4-yl)pyrido[2,3-b]pyrazin-6-amine (compound Y) or a pharmaceutically acceptable salt thereof or a solvate thereof, and their chemical synthesis are described in WO2011/135376 and WO2013/061080, which are incorporated herein by reference. They are described as inhibitors or modulators of the activity of certain protein tyrosine kinases, in particular FGFR, and thus the compounds are useful in the treatment or prophylaxis, in particular the treatment, of disease states or conditions mediated by those tyrosine kinases, in particular FGFR. The compounds are useful in the treatment or prophylaxis, in particular the treatment, of cancer.

In WO2011/135376 present compound X is also exemplified as a hydrochloride salt. In WO2013/061080 present compound Y is also exemplified as a sulfate salt, as a hydrochloride salt, as a phosphate salt, as a lactate salt, as a fumarate salt.

The FGFR kinase inhibitors compound X and Y described herein have a differentiated selectivity profile which provides a new opportunity to use these targeted agents in patient sub-groups whose disease is driven by FGFR deregulation. The FGFR kinase inhibitors compound X and Y described herein exhibit reduced inhibitory action on additional kinases, particularly VEGFR, more in particular VEGFR2, and PDGFR, in particular PDGFR-beta, and offer the opportunity to have a differentiated side-effect or toxicity profile and as such allow for a more effective treatment of these indications. Inhibitors of VEGFR2 and PDGFR-beta are associated with toxicities such as hypertension or oedema respectively. In the case of VEGFR2 inhibitors this hypertensive effect is often dose limiting, may be contraindicated in certain patient populations and requires clinical management. The FGFR kinase inhibitors compound X and Y described herein are FGFR1, 2, 3 and 4 inhibitors.

Vascular Endothelial Growth Factor (VEGFR)

Vascular endothelial growth factor (VEGF), a polypeptide, is mitogenic for endothelial cells in vitro and stimulates angiogenic responses in vivo. VEGF has also been linked to inappropriate angiogenesis. VEGFR(s) are protein tyrosine kinases (PTKs). PTKs catalyze the phosphorylation of specific tyrosine residues in proteins involved in cell function thus regulating cell growth, survival and differentiation.

Three PTK receptors for VEGF have been identified: VEGFR-1 (Flt-1); VEGFR-2 (Flk-1 or KDR) and VEGFR-3 (Flt-4). These receptors are involved in angiogenesis and participate in signal transduction. Of particular interest is VEGFR-2, which is a transmembrane receptor PTK expressed primarily in endothelial cells. Activation of VEGFR-2 by VEGF is a critical step in the signal transduction pathway that initiates tumour angiogenesis. VEGF expression may be constitutive to tumour cells and can also be upregulated in response to certain stimuli. One such stimuli is hypoxia, where VEGF expression is upregulated in both tumour and associated host tissues. The VEGF ligand activates VEGFR-2 by binding with its extracellular VEGF binding site. This leads to receptor dimerization of VEGFRs and autophosphorylation of tyrosine residues at the intracellular kinase domain of VEGFR-2. The kinase domain operates to transfer a phosphate from ATP to the tyrosine residues, thus providing binding sites for signalling proteins downstream of VEGFR-2 leading ultimately to initiation of angiogenesis.

PDGFR

A malignant tumour is the product of uncontrolled cell proliferation. Cell growth is controlled by a delicate balance between growth-promoting and growth-inhibiting factors. In normal tissue the production and activity of these factors results in differentiated cells growing in a controlled and regulated manner that maintains the normal integrity and functioning of the organ. The malignant cell has evaded this control; the natural balance is disturbed (via a variety of mechanisms) and unregulated, aberrant cell growth occurs. A growth factor of importance in tumour development is the platelet-derived growth factor (PDGF) that comprises a family of peptide growth factors that signal through cell surface tyrosine kinase receptors (PDGFR) and stimulate various cellular functions including growth, proliferation, and differentiation.

*) BGJ398 (3-(2,6-dichloro-3,5-dimethoxyphenyl)-1-[6-[4-(4-ethylpiperazin-1-yl)anilino]pyrimidin-4-yl]-1-methylurea) having the following formula

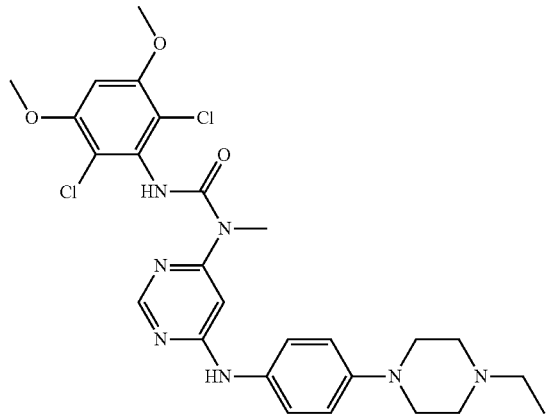 [SMILES: CCN1CCN(c2ccc(Nc3cc(N(C)C(=O)Nc4c(Cl)c(OC)cc(OC)c4Cl)ncn3)cc2)CC1]

*) AZD-4547 (N-(5-(3,5-dimethoxyphenethyl)-1H-pyrazol-3-yl)-4-((3S,5R)-3,5-dimethylpiperazin-1-yl)benzamide) having the following formula

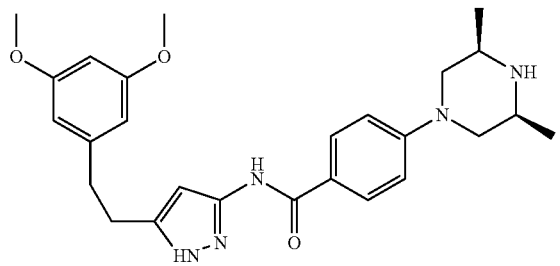 [SMILES: COc1cc(CCc2cc(NC(=O)c3ccc(N4C[C@@H](C)N[C@@H](C)C4)cc3)n[nH]2)cc(OC)c1]

*) PD 173074 (N-[2-[[4-(Diethylamino)butyl]amino]-6-(3,5-dimethoxyphenyl)pyrido[2,3-d]pyrimidin-7-yl]-N'-(1,1-dimethylethyl)urea) having the following formula

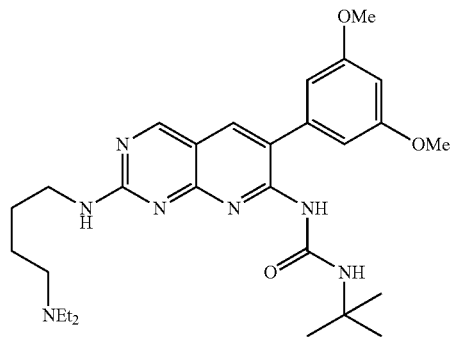

*) LY-2874455 ((R,E)-2-(4-(2-(5-(1-(3,5-dichloropyridin-4-yl)ethoxy)-1H-indazol-3-yl)vinyl)-1H-pyrazol-1-yl)ethanol) having the following formula

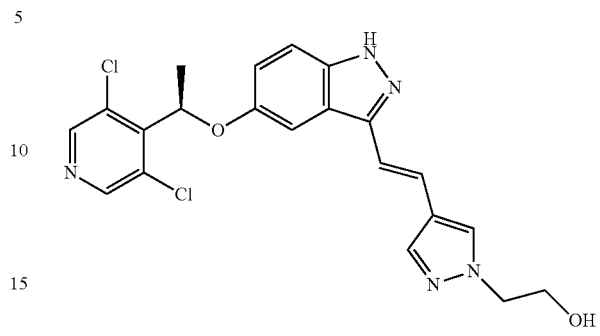

*) Brivanib (alaninate) (S)-(R)-1-((4-((4-fluoro-2-methyl-1H-indol-5-yl)oxy)-5-methylpyrrolo[2,1-f][1,2,4]triazin-6-yl)oxy)propan-2-yl 2-aminopropanoate.

*) Intedanib

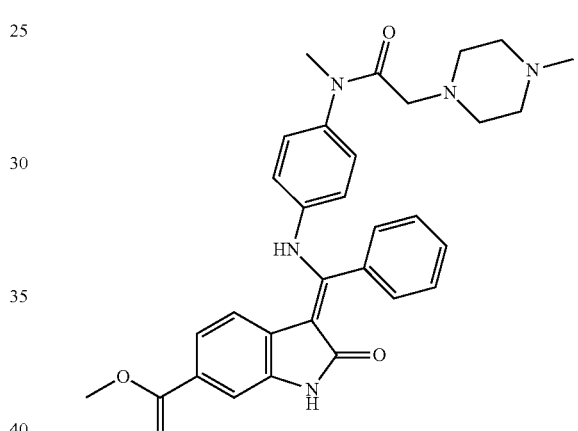

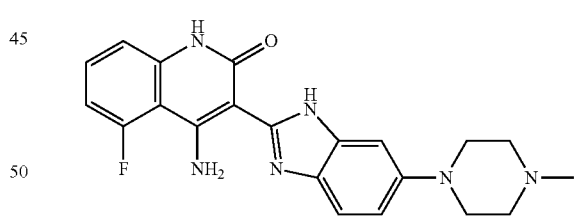

*) Dovitinib
*) Cediranib

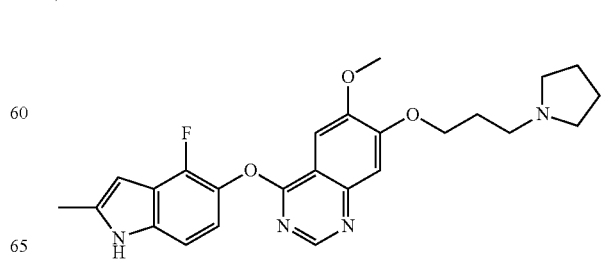

*) Masitinib

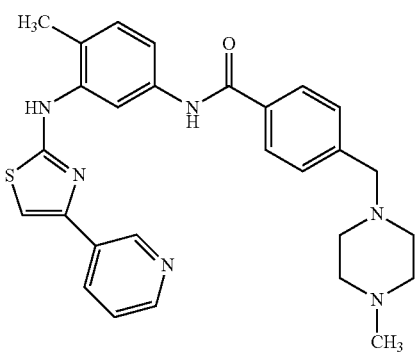 [SMILES: Cc1ccc(NC(=O)c2ccc(CN3CCN(C)CC3)cc2)cc1Nc1nc(-c2cccnc2)cs1]

*) Orantinib

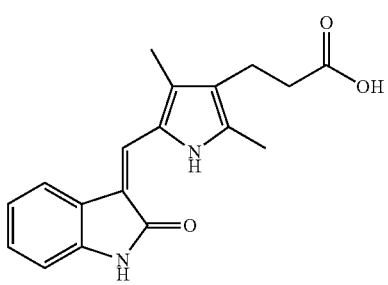 [SMILES: Cc1[nH]c(/C=C2\C(=O)Nc3ccccc32)c(C)c1CCC(=O)O]

*) Ponatinib (AP24534)

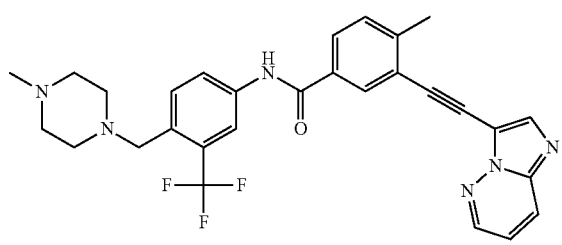 [SMILES: Cc1ccc(C(=O)Nc2ccc(CN3CCN(C)CC3)c(C(F)(F)F)c2)cc1C#Cc1cnc2cccnn12]

*) E-7080 (lenvatinib)

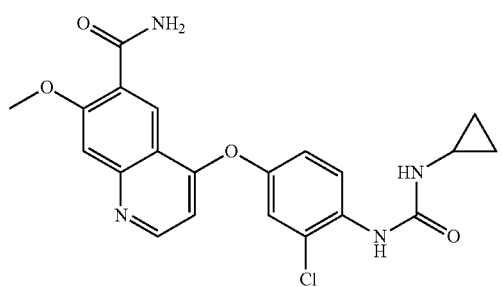 [SMILES: COc1cc2nccc(Oc3ccc(NC(=O)NC4CC4)c(Cl)c3)c2cc1C(N)=O]

*) E-3810 (luciatnib)

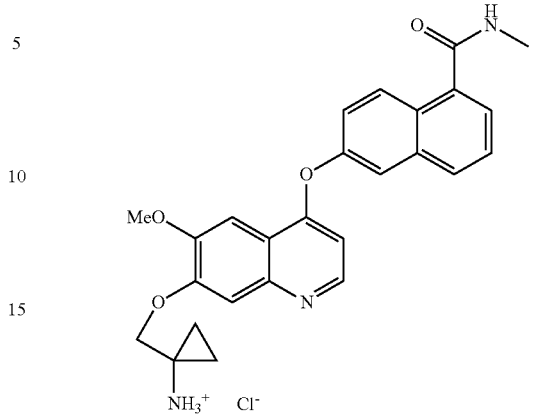

*) BAY 1163877, TAS-120, ARQ087, ASP5878, FF284,
*) Antibodies or related compounds, such as for example HGS1036/FP-1039; MFGR1877S; AV-370; GP369/AV-396b; HuGAL-FR21; monoclonal antibodies (BAY 1179470, RG-7444)

Further useful agents for the combinations as described herein include verapamil, a calcium antagonist found to be useful in combination with antineoplastic agents to establish chemosensitivity in tumor cells resistant to accepted chemotherapeutic agents and to potentiate the efficacy of such compounds in drug-sensitive malignancies. See Simpson W G, The calcium channel blocker verapamil and cancer chemotherapy. Cell Calcium. 1985 December; 6(6):449-67. Additionally, yet to emerge chemotherapeutic agents are contemplated as being useful in combination with the compound of the present invention.

In another embodiment of the present invention, the compound of the present invention may be administered in combination with radiation therapy. As used herein, "radiation therapy" refers to a therapy comprising exposing the subject in need thereof to radiation. Such therapy is known to those skilled in the art. The appropriate scheme of radiation therapy will be similar to those already employed in clinical therapies wherein the radiation therapy is used alone or in combination with other chemotherapeutics.

In another embodiment of the present invention, the compound of the present invention may be administered in combination with a gene therapy. As used herein, "gene therapy" refers to a therapy targeting on particular genes involved in tumor development. Possible gene therapy strategies include the restoration of defective cancer-inhibitory genes, cell transduction or transfection with antisense DNA corresponding to genes coding for growth factors and their receptors, RNA-based strategies such as ribozymes, RNA decoys, antisense messenger RNAs and small interfering RNA (siRNA) molecules and the so-called 'suicide genes'.

In other embodiments of this invention, the compound of the present invention may be administered in combination with an immunotherapy. As used herein, "immunotherapy" refers to a therapy targeting particular protein involved in tumor development via antibodies specific to such protein. For example, monoclonal antibodies against vascular endothelial growth factor have been used in treating cancers.

Where a second pharmaceutical is used in addition to the compound of the present invention, the two pharmaceuticals may be administered simultaneously (e.g. in separate or unitary compositions) sequentially in either order, at approximately the same time, or on separate dosing schedules. In the latter case, the two compounds will be administered within a period and in an amount and manner that is sufficient to ensure that an advantageous or synergistic effect is achieved. It will be appreciated that the preferred method and order of administration and the respective dosage amounts and regimes for each component of the combination will depend on the particular chemotherapeutic agent being administered in conjunction with the compound of the present invention, their route of administration, the particular tumor being treated and the particular host being treated.

As will be understood by those of ordinary skill in the art, the appropriate doses of chemotherapeutic agents will be generally similar to or less than those already employed in clinical therapies wherein the chemotherapeutics are administered alone or in combination with other chemotherapeutics.

The optimum method and order of administration and the dosage amounts and regime can be readily determined by those skilled in the art using conventional methods and in view of the information set out herein.

By way of example only, platinum compounds are advantageously administered in a dosage of 1 to 500 mg per square meter ($mg/m^2$) of body surface area, for example 50 to 400 $mg/m^2$, particularly for cisplatin in a dosage of about 75 $mg/m^2$ and for carboplatin in about 300 $mg/m^2$ per course of treatment. Cisplatin is not absorbed orally and must therefore be delivered via injection intravenously, subcutaneously, intratumorally or intraperitoneally.

By way of example only, taxane compounds are advantageously administered in a dosage of 50 to 400 mg per square meter ($mg/m^2$) of body surface area, for example 75 to 250 $mg/m^2$, particularly for paclitaxel in a dosage of about 175 to 250 $mg/m^2$ and for docetaxel in about 75 to 150 $mg/m^2$ per course of treatment.

By way of example only, camptothecin compounds are advantageously administered in a dosage of 0.1 to 400 mg per square meter ($mg/m^2$) of body surface area, for example 1 to 300 $mg/m^2$, particularly for irinotecan in a dosage of about 100 to 350 $mg/m^2$ and for topotecan in about 1 to 2 $mg/m^2$ per course of treatment.

By way of example only, *vinca* alkaloids may be advantageously administered in a dosage of 2 to 30 mg per square meter ($mg/m^2$) of body surface area, particularly for vinblastine in a dosage of about 3 to 12 $mg/m^2$, for vincristine in a dosage of about 1 to 2 $mg/m^2$, and for vinorelbine in dosage of about 10 to 30 $mg/m^2$ per course of treatment.

By way of example only, anti-tumor nucleoside derivatives may be advantageously administered in a dosage of 200 to 2500 mg per square meter ($mg/m^2$) of body surface area, for example 700 to 1500 $mg/m^2$. 5-fluorouracil (5-FU) is commonly used via intravenous administration with doses ranging from 200 to 500 $mg/m^2$ (preferably from 3 to 15 mg/kg/day). Gemcitabine is advantageously administered in a dosage of about 800 to 1200 $mg/m^2$ and capecitabine is advantageously administered in about 1000 to 2500 $mg/m^2$ per course of treatment.

By way of example only, alkylating agents may be advantageously administered in a dosage of 100 to 500 mg per square meter ($mg/m^2$) of body surface area, for example 120 to 200 $mg/m^2$, particularly for cyclophosphamide in a dosage of about 100 to 500 $mg/m^2$, for chlorambucil in a dosage of about 0.1 to 0.2 mg/kg of body weight, for carmustine in a dosage of about 150 to 200 $mg/m^2$, and for lomustine in a dosage of about 100 to 150 $mg/m^2$ per course of treatment.

By way of example only, podophyllotoxin derivatives may be advantageously administered in a dosage of 30 to 300 mg per square meter ($mg/m^2$) of body surface area, for example 50 to 250 $mg/m^2$, particularly for etoposide in a dosage of about 35 to 100 $mg/m^2$ and for teniposide in about 50 to 250 $mg/m^2$ per course of treatment.

By way of example only, anthracycline derivatives may be advantageously administered in a dosage of 10 to 75 mg per square meter ($mg/m^2$) of body surface area, for example 15 to 60 $mg/m^2$, particularly for doxorubicin in a dosage of about 40 to 75 $mg/m^2$, for daunorubicin in a dosage of about 25 to 45 $mg/m^2$, and for idarubicin in a dosage of about 10 to 15 $mg/m^2$ per course of treatment.

By way of example only, anti-estrogen compounds may be advantageously administered in a dosage of about 1 to 100 mg daily depending on the particular agent and the condition being treated. Tamoxifen is advantageously administered orally in a dosage of 5 to 50 mg, preferably 10 to 20 mg twice a day, continuing the therapy for sufficient time to achieve and maintain a therapeutic effect. Toremifene is advantageously administered orally in a dosage of about 60 mg once a day, continuing the therapy for sufficient time to achieve and maintain a therapeutic effect. Anastrozole is advantageously administered orally in a dosage of about 1 mg once a day. Droloxifene is advantageously administered orally in a dosage of about 20-100 mg once a day. Raloxifene is advantageously administered orally in a dosage of about 60 mg once a day. Exemestane is advantageously administered orally in a dosage of about 25 mg once a day.

By way of example only, biologics may be advantageously administered in a dosage of about 1 to 5 mg per square meter ($mg/m^2$) of body surface area, or as known in the art, if different. For example, trastuzumab is advantageously administered in a dosage of 1 to 5 $mg/m^2$ particularly 2 to 4 $mg/m^2$ per course of treatment.

Dosages may be administered, for example once, twice or more per course of treatment, which may be repeated for example every 7, 14, 21 or 28 days.

The compound of the present invention can be administered to a subject systemically, for example, intravenously, orally, subcutaneously, intramuscular, intradermal, or parenterally. The compound of the present invention can also be administered to a subject locally. Non-limiting examples of local delivery systems include the use of intraluminal medical devices that include intravascular drug delivery catheters, wires, pharmacological stents and endoluminal paving. In particular, the compound of the present invention is administered orally.

The compound of the present invention can further be administered to a subject in combination with a targeting agent to achieve high local concentration of the compound at the target site. In addition, the compound of the present invention may be formulated for fast-release or slow-release with the objective of maintaining the drugs or agents in contact with target tissues for a period ranging from hours to weeks.

The present invention also provides a pharmaceutical composition comprising a compound of formula (I) in association with a pharmaceutically acceptable carrier. The pharmaceutical composition may contain between about 0.1 mg and 1000 mg, preferably about 100 to 500 mg, of the compound, and may be constituted into any form suitable for the mode of administration selected.

The phrases "pharmaceutically acceptable" refer to molecular entities and compositions that do not produce an adverse, allergic or other untoward reaction when administered to an animal, or a human, as appropriate. Veterinary uses are equally included within the invention and "pharmaceutically acceptable" Compositions include compositions for both clinical and/or veterinary use.

Carriers include necessary and inert pharmaceutical excipients, including, but not limited to, binders, suspending agents, lubricants, flavorants, sweeteners, preservatives, dyes, and coatings. Compositions suitable for oral administration include solid forms, such as pills, tablets, caplets, capsules (each including immediate release, timed release and sustained release formulations), granules, and powders, and liquid forms, such as solutions, syrups, elixirs, emulsions, and suspensions. Forms useful for parenteral administration include sterile solutions, emulsions and suspensions.

The pharmaceutical composition of the present invention also includes a pharmaceutical composition for slow release of the compound of the present invention. The composition includes a slow release carrier (typically, a polymeric carrier) and a compound of the present invention.

Slow release biodegradable carriers are well known in the art. These are materials that may form particles that capture therein an active compound(s) and slowly degrade/dissolve under a suitable environment (e.g., aqueous, acidic, basic, etc) and thereby degrade/dissolve in body fluids and release the active compound(s) therein. The particles are preferably nanoparticles (i.e., in the range of about 1 to 500 nm in diameter, preferably about 50-200 nm in diameter, and most preferably about 100 nm in diameter).

The present invention also provides methods to prepare the pharmaceutical compositions of this invention. The compound of formula (I), as the active ingredient, is intimately admixed with a pharmaceutical carrier according to conventional pharmaceutical compounding techniques, which carrier may take a wide variety of forms depending on the form of preparation desired for administration, e.g., oral or parenteral such as intramuscular. In preparing the compositions in oral dosage form, any of the usual pharmaceutical media may be employed. Thus, for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules, caplets, gelcaps and tablets, suitable carriers and additives include starches, sugars, diluents, granulating agents, lubricants, binders, disintegrating agents and the like. Because of their ease in administration, tablets and capsules represent the most advantageous oral dosage unit form, in which case solid pharmaceutical carriers are obviously employed. If desired, tablets may be (sugar) coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. In preparation for slow release, for instance, a slow release carrier, typically a polymeric carrier, and a compound of the present invention are first dissolved or dispersed in an organic solvent. The obtained organic solution is then added into an aqueous solution to obtain an oil-in-water-type emulsion. Preferably, the aqueous solution includes surface-active agent(s). Subsequently, the organic solvent is evaporated from the oil-in-water-type emulsion to obtain a colloidal suspension of particles containing the slow release carrier and the compound of the present invention.

The pharmaceutical compositions herein will contain, per dosage unit, e.g., tablet, capsule, powder, injection, teaspoonful and the like, an amount of the active ingredient necessary to deliver an effective dose as described above. The pharmaceutical compositions herein will contain, per unit dosage unit, e.g., tablet, capsule, powder, injection, suppository, teaspoonful and the like, from about 0.01 mg to 200 mg/kg of body weight per day. Preferably, the range is from about 0.03 to about 100 mg/kg of body weight per day, most preferably, from about 0.05 to about 10 mg/kg of body weight per day. The compound may be administered on a regimen of 1 to 5 times per day. The dosages, however, may be varied depending upon the requirement of the patients, the severity of the condition being treated and the compound being employed. The use of either daily administration or post-periodic dosing may be employed.

Preferably these compositions are in unit dosage forms such as tablets, pills, capsules, powders, granules, sterile parenteral solutions or suspensions, metered aerosol or liquid sprays, drops, ampoules, auto-injector devices or suppositories; for oral parenteral, intranasal, sublingual or rectal administration, or for administration by inhalation or insufflation. Alternatively, the composition may be presented in a form suitable for once-weekly or once-monthly administration; for example, an insoluble salt of the active compound, such as the decanoate salt, may be adapted to provide a depot preparation for intramuscular injection. For preparing solid compositions such as tablets, the principal active ingredient is mixed with a pharmaceutical carrier, e.g. conventional tableting ingredients such as corn starch, lactose, sucrose, sorbitol, talc, stearic acid, magnesium stearate, dicalcium phosphate or gums, and other pharmaceutical diluents, e.g. water, to form a solid preFormulation composition containing a homogeneous mixture of a compound of the present invention, or a pharmaceutically acceptable salt thereof. When referring to these preFormulation compositions as homogeneous, it is meant that the active ingredient is dispersed evenly throughout the composition so that the composition may be readily subdivided into equally effective dosage forms such as tablets, pills and capsules. This solid preFormulation composition is then subdivided into unit dosage forms of the type described above containing from 0.1 to about 500 mg of the active ingredient of the present invention. The tablets or pills of the novel composition can be coated or otherwise compounded to provide a dosage form affording the advantage of prolonged action. For example, the tablet or pill can comprise an inner dosage and an outer dosage component, the latter being in the form of an envelope over the former. The two components can be separated by an enteric layer which serves to resist disintegration in the stomach and permits the inner component to pass intact into the duodenum or to be delayed in release. A variety of material can be used for such enteric layers or coatings, such materials including a number of polymeric acids with such materials as shellac, acetyl alcohol and cellulose acetate.

The liquid forms in which the compound of formula (I) may be incorporated for administration orally or by injection include, aqueous solutions, suitably flavored syrups, aqueous or oil suspensions, and flavored emulsions with edible oils such as cottonseed oil, sesame oil, coconut oil or peanut oil, as well as elixirs and similar pharmaceutical vehicles. Suitable dispersing or suspending agents for aqueous suspensions, include synthetic and natural gums such as tragacanth, acacia, alginate, dextran, sodium carboxymethylcellulose, methylcellulose, polyvinyl-pyrrolidone or gelatin. The liquid forms in suitably flavored suspending or dispersing agents may also include the synthetic and natural gums, for example, tragacanth, acacia, methyl-cellulose and the like. For parenteral administration, sterile suspensions and solutions are desired. Isotonic preparations which generally contain suitable preservatives are employed when intravenous administration is desired.

Advantageously, the compound of formula (I) may be administered in a single daily dose, or the total daily dosage may be administered in divided doses of two, three or four times daily. Furthermore, compounds for the present invention can be administered in intranasal form via topical use of suitable intranasal vehicles, or via transdermal skin patches well known to those of ordinary skill in that art. To be administered in the form of a transdermal delivery system, the dosage administration will, of course, be continuous rather than intermittent throughout the dosage regimen.

For instance, for oral administration in the form of a tablet or capsule, the active drug component can be combined with an oral, non-toxic pharmaceutically acceptable inert carrier such as ethanol, glycerol, water and the like. Moreover, when desired or necessary, suitable binders; lubricants, disintegrating agents and coloring agents can also be incorporated into the mixture. Suitable binders include, without limitation, starch, gelatin, natural sugars such as glucose or beta-lactose, corn sweeteners, natural and synthetic gums such as acacia, tragacanth or sodium oleate, sodium stearate, magnesium stearate, sodium benzoate, sodium acetate, sodium chloride and the like. Disintegrators include, without limitation, starch, methyl cellulose, agar, bentonite, xanthan gum and the like.

The daily dosage of the compound of the present invention may be varied over a wide range from 1 to 5000 mg per adult human per day. For oral administration, the compositions are preferably provided in the form of tablets containing, 0.01, 0.05, 0.1, 0.5, 1.0, 2.5, 5.0, 10.0, 15.0, 25.0, 50.0, 100, 150, 200, 250 and 500 milligrams of the active ingredient for the symptomatic adjustment of the dosage to the patient to be treated. An effective amount of the drug is ordinarily supplied at a dosage level of from about 0.01 mg/kg to about 200 mg/kg of body weight per day. Particularly, the range is from about 0.03 to about 100 mg/kg or from about 0.03 to about 15 mg/kg of body weight per day, and more particularly, from about 0.05 to about 10 mg/kg of body weight per day. The compound of the present invention may be administered on a regimen up to four or more times per day, preferably of 1 to 2 times per day.

Optimal dosages to be administered may be readily determined by those skilled in the art, and will vary with the particular compound used, the mode of administration, the strength of the preparation, the mode of administration, and the advancement of the disease condition. In addition, factors associated with the particular patient being treated, including patient age, weight, diet and time of administration, will result in the need to adjust dosages.

The compounds of the present invention can also be administered in the form of liposome delivery systems, such as small unilamellar vesicles, large unilamellar vesicles, and multilamellar vesicles. Liposomes can be formed from a variety of lipids, including but not limited to amphipathic lipids such as phosphatidylcholines, sphingomyelins, phosphatidylethanolamines, phophatidylcholines, cardiolipins, phosphatidylserines, phosphatidylglycerols, phosphatidic acids, phosphatidylinositols, diacyl trimethylammonium propanes, diacyl dimethylammonium propanes, and stearylamine, neutral lipids such as triglycerides, and combinations thereof. They may either contain cholesterol or may be cholesterol-free.

The compound of the present invention can also be administered locally. Any delivery device, such as intravascular drug delivery catheters, wires, pharmacological stents and endoluminal paving, may be utilized. The delivery system for such a device may comprise a local infusion catheter that delivers the compound at a rate controlled by the administrator.

The present invention provides a drug delivery device comprising an intraluminal medical device, preferably a stent, and a therapeutic dosage of a compound of the invention.

The term "stent" refers to any device capable of being delivered by a catheter. A stent is routinely used to prevent vascular closure due to physical anomalies such as unwanted inward growth of vascular tissue due to surgical trauma. It often has a tubular, expanding lattice-type structure appropriate to be left inside the lumen of a duct to relieve an obstruction. The stent has a lumen wall-contacting surface and a lumen-exposed surface. The lumen-wall contacting surface is the outside surface of the tube and the lumen-exposed surface is the inner surface of the tube. The stent can be polymeric, metallic or polymeric and metallic, and it can optionally be biodegradable.

Commonly, stents are inserted into the lumen in a non-expanded form and are then expanded autonomously, or with the aid of a second device in situ. A typical method of expansion occurs through the use of a catheter-mounted angioplasty balloon which is inflated within the stenosed vessel or body passageway in order to shear and disrupt the obstructions associated with the wall components of the vessel and to obtain an enlarged lumen. Self-expanding stents as described in U.S. Pat. No. 6,776,796 (Falotico et al.) may also be utilized. The combination of a stent with drugs, agents or compounds that prevent inflammation and proliferation, may provide the most efficacious treatment for post-angioplastry restenosis.

The compound of formula (I) can be incorporated into or affixed to the stent in a number of ways and in utilizing any number of biocompatible materials. In one exemplary embodiment, the compound is directly incorporated into a polymeric matrix, such as the polymer polypyrrole, and subsequently coated onto the outer surface of the stent. The compound elutes from the matrix by diffusion through the polymer. Stents and methods for coating drugs on stents are discussed in detail in the art. In another exemplary embodiment, the stent is first coated with as a base layer comprising a solution of the compound, ethylene-co-vinylacetate, and polybutylmethacrylate. Then, the stent is further coated with an outer layer comprising only polybutylmethacrylate. The outlayer acts as a diffusion barrier to prevent the compound from eluting too quickly and entering the surrounding tissues.

The thickness of the outer layer or topcoat determines the rate at which the compound elutes from the matrix. Stents and methods for coating are discussed in detail in WIPO publication WO9632907, U.S. Publication No. 2002/0016625 and references disclosed therein.

The solution of the compound of the invention and the biocompatible materials/polymers may be incorporated into or onto a stent in a number of ways. For example, the solution may be sprayed onto the stent or the stent may be dipped into the solution. In a preferred embodiment, the solution is sprayed onto the stent and then allowed to dry. In another exemplary embodiment, the solution may be electrically charged to one polarity and the stent electrically changed to the opposite polarity. In this manner, the solution and stent will be attracted to one another. In using this type of spraying process, waste may be reduced and more control over the thickness of the coat may be achieved. Compound is preferably only affixed to the outer surface of the stent that makes contact with one tissue. However, for some compounds, the entire stent may be coated. The combination of the dose of compound applied to the stent and the polymer coating that controls the release of the drug is important in the effectiveness of the drug. The compound preferably remains on the stent for at least three days up to approximately six months and more, preferably between seven and thirty days.

Any number of non-erodible biocompatible polymers may be utilized in conjunction with the compound of the invention. It is important to note that different polymers may be utilized for different stents. For example, the above-described ethylene-co-vinylacetate and polybutylmethacrylate matrix works well with stainless steel stents. Other polymers may be utilized more effectively with stents formed from other materials, including materials that exhibit superelastic properties such as alloys of nickel and titanium.

Restenosis is responsible for a significant morbidity and mortality following coronary angioplasty. Restenosis occurs through a combination of four processes including elastic recoil, thrombus formation, intima hyperplasia and extracellular matrix remodeling. Several growth factors have been recently identified to play a part in these processes leading to restenosis. See Schiele T M et. al., 2004, "Vascular restenosis—striving for therapy." Expert Opin Pharmacother. 5(11):2221-32. Vascular smooth muscle cells (VSMC) express c-Met receptor. Exposure to hepatocyte growth factor, the ligand for c-Met, stimulates these cells to exhibit a migratory phenotype. See Taher et. al., Hepatocyte growth factor triggers signaling cascades mediating vascular smooth muscle cell migration. *Biochem Biophys Res Commun.* (2002) 298(1):80-6; Morishita R, Aoki M, Yo Y, Ogihara T. Hepatocyte growth factor as cardiovascular hormone: role of HGF in the pathogenesis of cardiovascular disease. Endocr J. (2002) June; 49(3):273-84. Since VSMC migration from the media to the intima of arteries plays a role in the development of atherosclerosis and restenosis, antagonists of c-Met kinase activity are believed to present a viable therapeutic strategy in the treatment of these diseases.

Accordingly, the present invention provides a method for the treatment of disorders related to c-Met, including restenosis, intimal hyperplasia or inflammation, in blood vessel walls, comprising the controlled delivery, by release from an intraluminal medical device, such as a stent, of the compound of the invention in therapeutically effective amounts. The present invention also provides for the compound of formula (I) for use in the treatment of disorders related to c-Met, including restenosis, intimal hyperplasia or inflammation, in blood vessel walls.

Methods for introducing a stent into a lumen of a body are well known and the compound-coated stents of this invention are preferably introduced using a catheter.

As will be appreciated by those of ordinary skill in the art, methods will vary slightly based on the location of stent implantation. For coronary stent implantation, the balloon catheter bearing the stent is inserted into the coronary artery and the stent is positioned at the desired site. The balloon is inflated, expanding the stent. As the stent expands, the stent contacts the lumen wall. Once the stent is positioned, the balloon is deflated and removed. The stent remains in place with the lumen-contacting surface bearing the compound directly contacting the lumen wall surface. Stent implantation may be accompanied by anticoagulation therapy as needed.

Optimum conditions for delivery of the compound for use in the stent of the invention may vary with the different local delivery systems used, as well as the properties and concentrations of the compounds used. Conditions that may be optimized include, for example, the concentrations of the compounds, the delivery volume, the delivery rate, the depth of penetration of the vessel wall, the proximal inflation pressure, the amount and size of perforations and the fit of the drug delivery catheter balloon. Conditions may be optimized for inhibition of smooth muscle cell proliferation at the site of injury such that significant arterial blockage due to restenosis does not occur, as measured, for example, by the proliferative ability of the smooth muscle cells, or by changes in the vascular resistance or lumen diameter. Optimum conditions can be determined based on data from animal model studies using routine computational methods.

Another alternative method for administering compounds of this invention may be by conjugating the compound to a targeting agent which directs the conjugate to its intended site of action, i.e., to vascular endothelial cells, or to tumor cells. Both antibody and non-antibody targeting agents may be used. Because of the specific interaction between the targeting agent and its corresponding binding partner, a compound of the present invention can be administered with high local concentrations at or near a target site and thus treats the disorder at the target site more effectively.

The antibody targeting agents include antibodies or antigen-binding fragments thereof, that bind to a targetable or accessible component of a tumor cell, tumor vasculature, or tumor stroma. The "targetable or accessible component" of a tumor cell, tumor vasculature or tumor stroma, is preferably a surface-expressed, surface-accessible or surface-localized component. The antibody targeting agents also include antibodies or antigen-binding fragments thereof, that bind to an intracellular component that is released from a necrotic tumor cell. Preferably such antibodies are monoclonal antibodies, or antigen-binding fragments thereof, that bind to insoluble intracellular antigen(s) present in cells that may be induced to be permeable, or in cell ghosts of substantially all neoplastic and normal cells, but are not present or accessible on the exterior of normal living cells of a mammal. In the present invention, the targetable or accessible component might be the c-Met receptor as it is accessible and expressed on or near the target tissues.

As used herein, the term "antibody" is intended to refer broadly to any immunologic binding agent such as IgG, IgM, IgA, IgE, F(ab')2, a univalent fragment such as Fab', Fab, Dab, as well as engineered antibodies such as recombinant antibodies, humanized antibodies, bispecific antibodies, and the like. The antibody can be either the polyclonal or the monoclonal, although the monoclonal is preferred. There is a very broad array of antibodies known in the art that have immunological specificity for the cell surface of virtually any solid tumor type (see a Summary Table on monoclonal antibodies for solid tumors in U.S. Pat. No. 5,855,866 to Thorpe et al). Methods are known to those skilled in the art to produce and isolate antibodies against tumor (U.S. Pat. No. 5,855,866 to Thorpe et al., and U.S. Pat. No. 6,342,219 to Thorpe et al.).

Techniques for conjugating therapeutic moiety to antibodies are well known, see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56 (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987); Thorpe, "Antibody Carriers Of Cytotoxic Agents In Cancer Therapy: A Review", in Monoclonal Antibodies '84: Biological And Clinical Applications, Pinchera et al. (eds.), pp. 475-506 (1985). Similar techniques can also be applied to attach compounds of the invention to non-antibody targeting agents. Those skilled in the art will know, or be able to determine, methods of forming conjugates with non-antibody targeting agents, such as small molecules, oligopeptides, polysaccharides, or other polyanionic compounds.

Although any linking moiety that is reasonably stable in blood, can be used to link the compounds of the present invention to the targeting agent, biologically-releasable bonds and/or selectively cleavable spacers or linkers are preferred. "Biologically-releasable bonds" and "selectively cleavable spacers or linkers" still have reasonable stability in the circulation, but are releasable, cleavable or hydrolysable only or preferentially under certain conditions, i.e., within a certain environment, or in contact with a particular agent. Such bonds include, for example, disulfide and trisulfide bonds and acid-labile bonds, as described in U.S. Pat. Nos. 5,474,765 and 5,762,918 and enzyme-sensitive bonds, including peptide bonds, esters, amides, phosphodiesters and glycosides as described in U.S. Pat. Nos. 5,474,765 and 5,762,918. Such selective-release design features facilitate sustained release of the compounds from the conjugates at the intended target site.

The present invention provides a pharmaceutical composition comprising an effective amount of a compound of the present invention conjugated to a targeting agent and a pharmaceutically acceptable carrier.

The present invention further provides a method of treating of a disorder related to c-Met, particularly a tumor, comprising administering to a subject a therapeutically effective amount of a compound of formula (I) conjugated to a targeting agent. The present invention further provides for the compound of formula (I) conjugated to a targeting agent for use in the treatment of a disorder related to c-Met, particularly a tumor. The present invention further provides for the use of a compound of formula (I) conjugated to a targeting agent for the preparation of a medicament for the treatment of a disorder related to c-Met, particularly a tumor.

When proteins such as antibodies or growth factors, or polysaccharides are used as targeting agents, they are preferably administered in the form of injectable compositions. The injectable antibody solution will be administered into a vein, artery or into the spinal fluid over the course of from 2 minutes to about 45 minutes, preferably from 10 to 20 minutes. In certain cases, intradermal and intracavitary administration are advantageous for tumors restricted to areas close to particular regions of the skin and/or to particular body cavities. In addition, intrathecal administrations may be used for tumors located in the brain.

Therapeutically effective dose of the compound of the present invention conjugated to a targeting agent depends on the individual, the disease type, the disease state, the method of administration and other clinical variables. The effective dosages are readily determinable using data from an animal model. Experimental animals bearing solid tumors are frequently used to optimize appropriate therapeutic doses prior to translating to a clinical environment. Such models are known to be very reliable in predicting effective anti-cancer strategies. For example, mice bearing solid tumors, are widely used in pre-clinical testing to determine working ranges of therapeutic agents that give beneficial anti-tumor effects with minimal toxicity.

HGF/MET pathway has been implicated in inducing a more immunosuppressive tumor microenvironment directly by regulating T cell activity as well as indirectly by inducing enzymes responsible for T cell anergy. Met pathway inhibition by the compound of formula (I) may therefore prime immune response to checkpoint blocking agents (checkpoint blocking agents include for examples blocking agents of PD-1 and CTLA-4) as well as alleviate tumor induced immuno suppression and activate host immune response.

While the foregoing specification teaches the principles of the present invention, with examples provided for the purpose of illustration, it will be understood that the practice of the invention encompasses all of the usual variations, adaptations and/or modifications as come within the scope of the following claims and their equivalents.

The invention claimed is:

1. A compound of formula (I)

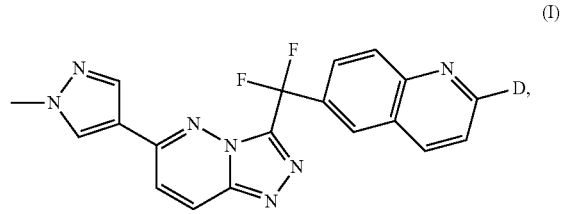

a N-oxide, a pharmaceutically acceptable salt or solvate thereof, wherein D represents deuterium and wherein the deuterium content in the 2-position of the quinoline at the D position is at least 50%.

2. The compound according to claim 1, wherein the compound is

base.

3. The compound according to claim 1, wherein the deuterium content in the 2-position of the quinoline at the D position is at least 93%.

4. The compound according to claim 3, wherein the deuterium content in the 2-position of the quinoline at the D position is at least 95%.

5. The compound according to claim 4, wherein the deuterium content in the 2-position of the quinoline at the D position is at least 98%.

6. A pharmaceutical composition comprising a pharmaceutically acceptable carrier, and as active ingredient a therapeutically effective amount of the compound of claim 1.

7. A process of preparing the compound of claim 1, the process comprising:
reductive deuteration of an intermediate of formula (II) wherein $W_1$ represents chloro, bromo or iodo in the presence of deuterium gas and in the presence of a suitable catalyst, a suitable solvent or solvent mixture, and a suitable base,

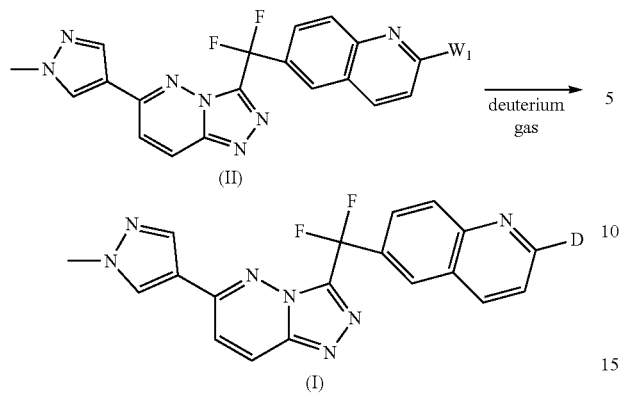

wherein D represents deuterium;
optionally, converting the compound of formula (I), into a therapeutically active non-toxic acid addition salt by treatment with an acid, or conversely, converting the acid addition salt form into a free base by treatment with alkali, or, optionally, preparing, solvates or N-oxide forms thereof.

8. A combination of the compound of claim 1 and another chemotherapeutic agent.

9. The combination according to claim 8, wherein the chemotherapeutic agent is a kinase inhibitor.

10. The combination according to claim 9, wherein the kinase inhibitor is a fibroblast growth factor receptor (FGFR) inhibitor.

11. The combination according to claim 8, wherein the chemotherapeutic agent is a platinum containing anti-cancer drug.

12. The compound according to claim 3, wherein the compound is

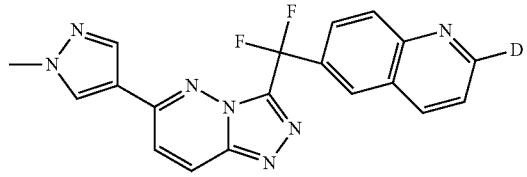 [SMILES: [2H]c1ccc2cc(C(F)(F)c3nnc4ccc(-c5cnn(C)c5)nn34)ccc2n1]

base.

13. The compound according to claim 4, wherein the compound is

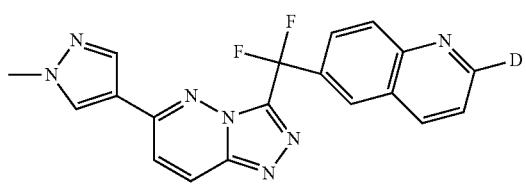 [SMILES: [2H]c1ccc2cc(C(F)(F)c3nnc4ccc(-c5cnn(C)c5)nn34)ccc2n1]

base.

14. The compound according to claim 5, wherein the compound is

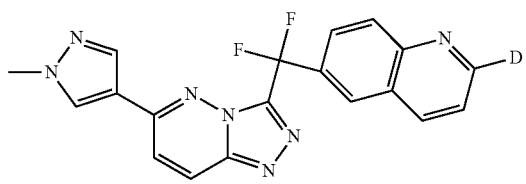 [SMILES: [2H]c1ccc2cc(C(F)(F)c3nnc4ccc(-c5cnn(C)c5)nn34)ccc2n1]

base.

15. The compound according to claim 1, wherein the deuterium content in the 2-position of the quinoline at the D position is at least 60%.

16. The compound according to claim 1, wherein the deuterium content in the 2-position of the quinoline at the D position is at least 70%.

17. The compound according to claim 1, wherein the deuterium content in the 2-position of the quinoline at the D position is at least 80%.

* * * * *

UNITED STATES PATENT AND TRADEMARK OFFICE
CERTIFICATE OF CORRECTION

PATENT NO. : 10,138,246 B2  
APPLICATION NO. : 15/531780  
DATED : November 27, 2018  
INVENTOR(S) : Patrick Blasius Furer et al.

Page 1 of 1

It is certified that error appears in the above-identified patent and that said Letters Patent is hereby corrected as shown below:

In the Specification

Column 3, Line 25:
"6-{Difluoro[6-(1-methyl-H-pyrazol-4-yl)[1,2,4]triazolo[4,"
Should read:
--6-{Difluoro[6-(1-methyl-1H-pyrazol-4-yl)[1,2,4]triazolo[4,--; and Column 20, Line 19:
"Column Agilent Eclipse Plus, C18 4.6 × 100 mm, 3.5 um"
Should read:
--Column Agilent Eclipse Plus, C18 4.6 × 100 mm, 3.5 μm--; and Column 29, Line 11:
"peridol, imatinib mesylate, gefitinib); famesyltransferse"
Should read:
--peridol, imatinib mesylate, gefitinib); farnesyltransferse--.

Signed and Sealed this  
Sixteenth Day of April, 2019

Andrei Iancu  
*Director of the United States Patent and Trademark Office*